US006849780B2

(12) United States Patent
Boeshore et al.

(10) Patent No.: US 6,849,780 B2
(45) Date of Patent: Feb. 1, 2005

(54) PLANTS RESISTANT TO CUCUMBER MOSAIC VIRUS STRAIN V34

(75) Inventors: Maury L. Boeshore, Wauconda, IL (US); J. Russell McMaster, Kenosha, WI (US); David M. Tricoli, Davis, CA (US); John F. Reynolds, Davis, CA (US); Kim J. Carney, Davis, CA (US)

(73) Assignee: Seminis Vegetable Seeds, Inc., Oxnard, CA (US)

( * ) Notice: Subject to any disclaimer, the term of this patent is extended or adjusted under 35 U.S.C. 154(b) by 259 days.

(21) Appl. No.: 10/011,033

(22) Filed: Nov. 13, 2001

(65) Prior Publication Data

US 2002/0124286 A1 Sep. 5, 2002

Related U.S. Application Data

(62) Division of application No. 09/616,567, filed on Jul. 14, 2000, now Pat. No. 6,342,655, which is a division of application No. 08/875,233, filed as application No. PCT/US95/07234 on Jun. 7, 1995, now Pat. No. 6,127,601, which is a continuation of application No. 08/367,789, filed on Dec. 30, 1994, now abandoned.

(51) Int. Cl.$^7$ ..................... C12N 15/82; C12N 15/33; C12N 5/10; C12N 15/90; A01H 5/00
(52) U.S. Cl. .................. 800/280; 435/320.1; 435/419; 435/468; 435/471; 536/23.72; 800/317
(58) Field of Search .................... 435/320.1, 419, 435/468, 471, 476; 536/23.72; 800/278–280, 295, 298, 301, 317

(56) References Cited

U.S. PATENT DOCUMENTS

| | | | |
|---|---|---|---|
| 5,349,128 A | 9/1994 | Quemada et al. | 800/280 |
| 5,623,066 A | 4/1997 | Quemada et al. | 536/23.72 |
| 5,633,434 A | 5/1997 | Schneider et al. | 800/278 |
| 5,739,082 A | 4/1998 | Donn | 504/206 |
| 5,792,926 A | 8/1998 | Schneider et al. | 800/280 |

FOREIGN PATENT DOCUMENTS

| | | | |
|---|---|---|---|
| EP | 0 412 912 A1 | 9/1990 | C12N/15/82 |
| EP | 0480310 A2 | 4/1992 | C12N/15/82 |
| WO | WO89/05858 | 6/1989 | C12N/15/00 |
| WO | WO90/02184 | 3/1990 | C12N/15/40 |
| WO | WO90/02185 | 3/1990 | C12N/15/40 |
| WO | WO91/04332 | 4/1991 | C12N/15/82 |

OTHER PUBLICATIONS

Francki et al., 1979 Commonwealth Agriculture Bureau Association of Applied Biologists, Cucumber Mosaic Virus, *CMI AAB Descriptions of Plant Viruses* Jul. 1979, No. 213 (No. 1 revised).

An, Gynheung, "Development of Plant Promoter Expression Vectorws and their Use for Analysis of Differential Activity of Nopaline Synthase Promoter in Transformed Tobacco Cells", *Plant Physiol.* 81:86–91 (1986).

Gould, Allan R., et al., "Cucumber Mosaic Virus RNA 3", *Eur. J. Biochem.*, 126:217–226 (Mar. 31, 1982).

Gonsalves, Dennis, et al., "Comparison of coat protein–mediated and genetically–derived resistance in cucumbers to infection by cucumber mosiac virus under field conditions with natural challenge inoculations by vectors", *Biotechnology*, 10:1562–1570 (1992).

Quemada, Hector D., et al., "Expression of Coat Protein Gene from Cucumber Masaic Virus Strain C, in Tobacco: Protection Against Infections by CMV Strains transmitted Mechanically or by Aphids", *Phytopathology* vol. 81(7):794–802 (1991).

Namba Shigetou, et al., "Protection of Transgenic Plants Expressing the Coat Protein Gene of Watermelon Mosaic Virus II or Zucchini Yellow Mosaic Virus Against Six Potyviruses", *Phytopathology*, vol. 82, No. 9, pp. 940–946, 1992.

Fromm, Michael et al., "Expression of genes transferred into monocot and dicot plant cells by electroporation", *Proc. Natl. Acad. Sci. USA* vol. 82:5824–5828, Sep. 1985 Genetics.

Zaitlin, Milton, et al., "Specificity of Replicase–Mediated Resistance to Cucumber Mosaic Virus", *Virology* 201:200–205 (1994).

Gordon, Karl H.J. et al., "Highly Purified Cucumber Mosaic Virus–induced RNA–Dependent RNA Polymerase Does Not Contain Any of the Full Length Translation Products of the Genomic RNSs", *Virology* 123:284–295 (1982).

Habii, N. et al., "Comparative Studies on Tomato Aspermy and Cucumber Mosaic Viruses", *Virology* 57:392–401 (1974).

Penden, K.W.C. et al., "Cucumber Mosaic Virus Contains a Functionally Divided Genome", *Virology* 53:487–492 (1973).

Bevan, Michael, et al., "Structure and transcription o f the nopaline synthase gene region of I–DNA", *Nucleic Acids Research*, vol. No. 2, pp. 369–385 (1983).

Smith, C.J.S. et al., "Antisense RNA inhibition of polygalacturonase gene expression in transgenic tomatoes", *Nature* vol. 334, 25, pp. 724–726 (Aug. 1988).

Klein, T.M., et al., "High–velocity microprojectiles for delivering nucleic acids into living cells", *Nature*, 327(7):70–73, May 1987.

Alexander R. van der Krol, Peter E. Lenting, Jetty Veenstra, Ingrid M. van der Meer, Ronald E. Koes, Anton G.M. Gerats, Joseph N.M. Mol & Antoine R. Stuitje, *Nature* 333(30):866–869, Jun. 1988.

(List continued on next page.)

*Primary Examiner*—Ashwin Mehta
(74) *Attorney, Agent, or Firm*—McDonough Holland & Allen PC

(57) ABSTRACT

The CP gene of CMV strain V34 (CMV–V34) is provided.

21 Claims, 33 Drawing Sheets

OTHER PUBLICATIONS

Paszkowski, Jerzy et al., "Potykus, Direct gene transfer to plants", *IRL Press Limited*, Oxford, England, pp. 2717–2722.

Tricoli, et al., Transgenic Squash Plants Exhibit Coat Protein Mediated Protection under Field Conditions, *J. Cell Biochem. Suppl.* 16F, 222 (1992), Abstract.

Tricoli, et al., "Asgrow Seed Company, Field trial results of transgenic squash and cantaloupe plants containing multiple virus resistance", *J. Cell. Biochem. Suppl.* 18A, p. 91, Abstract XI–126 (1994).

Namba, Shigetou, et al., "Expression of the gene encoding the coat protein of cucumber mosaic virus (CMV) strain WL appears to provide protection to tobacco plants against infection by several different CMV strains", *Gene*, 107:181–188 (1991).

Slightom, Jeffrey L., et al., "Custom polymerase–chain–reaction engineering of a plant expression vector", *Gene* vol. 102 251–255 (1991).

Hayakawa, Takaki et al., "Nucleotide sequence analysis of cDNA encoding the coat protein of cucumber mosaic virus: genome organization and molecular features of the protein," *Gene*, 71:107–114 (1988).

Nakajima, Midori, et al., "Protection against cucumber mosaic virus (CMV) strains O and Y and chrysanthemum mild mottle virus in transgenic tobacco plants expressing CMV–O coat protein", *Journal of General Virology*, 74:319–322 (1993).

Shintaku, Michael, "Coat protein gene sequencs of two cucumber mosaic virus strains reveals a single amino acid change correlating with chlorosis induction", *Journal of General Virology*, 72:2587–2589 (1991).

Owen, Judith, et al., "Nucleotide sequence and evolutionary relationships of cucumber mosaic virus (CMV) strains: CMV RNA 3", *J. Gen. Virol.* 71:2243–2249 (1990).

Quemada, Hector, et al., "Nucleotide Sequences of the Coat Protein Genes and Ranking Regions of Cucumber Mosaic Virus Strains C and WL RNA3", *J. Gen. Virol.* 1065–1073 (1989).

Hayakawa, Takahiko et al., "Complete Nucleotide Sequence of RNA 3 from Cucumber Mosaic Virus (CMV) Strain O: comparative Study of Nucleotide Sequences and Amino Acid among CMV Strains O, Q, D and Y", *J. Gen. Virol.* 70:499–504 (1989).

Clark, M.F. et al., "Characteristics of the Microplate Method of Enzyme–Linked immunosorbent Assay for the Detection of Plant Viruses", *J. Gen. Virol.* (1997) 34, 475–483.

Allmansberger, et al., "Genes for Gentamicin–(3)–N–acetyl–transferases III and IV. II. Nucleotide sequences of three AAC (3)–LH genes and Evolutionary Aspects", *Mol. Gen. Genet.* 198:514–520 (1985).

Kay, Robert, et al., "Hybrid pUC vectors for addition of new restriction enzyme sites to the ends of DNA fragments", *Nucleic Acids Research*, vol. 15, No. 6, 1987, p. 2778.

Carlberg, Carsten, et al., "Sequencing refractory GC rich regions in plasmid DNA", *Nucleic Acids Research*, vol. 15, No. 6, 1987, p. 2779.

Crossway, Anne, et al., "Integration of foreign DNA following microinjection of tobacco mesophyll protoplasts", *Mol. Gen. Genet.* (1986) 202:179–185.

EMBL ACC No. M98501 (Aug. 13, 1992).

DeBLas, C. et al., *J. Phytopatholoyg*, 141:323–329 (1994).

Anderson, et al.*Phytopathology*, 79:1284–1290 (1989).

GenBank Accession J02059 (Aug. 2, 1993).

Cuzzo, et al., *Bio Technology*, 6:549–557 (1988).

Nejidat, A., et al., *Physiologia Plantarum*, vol. 80:662–668 (1990).

Yie, Y., et al., *Molecular Plant–Microbe Interactions*, 5(6):460–465 (1992).

Okuno, T., et al., *Phytopathology*, 83(5):542–547 (1993).

Xue, B., et al., *Plant Disease*, 78(11):1038–1041 (1994).

Gonsalves, C., et al., *J. Amer. Soc. Hort. Sci.*, 119(2):345–355 (1994).

Liang, X., et al., *Plant Cell Reports*, 14:141–144 (1994).

Provvidenti, R., et al., *The Journal of Heredity*, 86(2):85–88 (Mar/Apr. 1995).

Chen, B., et al.,*Journal of General Virology*, 76(4):971–973 (1995).

Turner, N., et al., *Plant Molecular Biology*, edited by von Wettstein, D., et al., Plenum Press, pp. 351–356 (1987).

Hu, J.S., et al., *Plant Disease*, 79(9):902–906 (1995).

Suzuki, M., et al., *Journal of General Virology*, 76:1791–1799 (1995).

Perry, K., et al., *Virology*, 205:591–595 (1994).

FIG. 1A

```
  1  CCATGGACAAATCTGAATCAACCAGTGCTGGTCGTAACCGTCGGCGTCGTCCGCGTCGTG    60
     MetAspLysSerGluSerThrSerAlaGlyArgAsnArgArgArgArgProArgArgG
      M   D   K   S   E   S   T   S   A   G   R   N   R   R   R   R   P   R   R   G

61  GTTCCCGCTCCGCCTCCTCCTCCTCGGATGCTAACTTTAGAGTCTTGTCGCAGCAGCTTT   120
     lySerArgSerAlaSerSerSerAspAlaAsnPheArgValLeuSerGlnGlnLeuS
      S   R   S   A   S   S   S   S   D   A   N   F   R   V   L   S   Q   Q   L   S

121  CGCGACTTAACAAGACGTTAGCAGCTGGTCGTCCAACTATTAACCACCCAACCTTTGTAG   180
     erArgLeuAsnLysThrLeuAlaAlaGlyArgProThrIleAsnHisProThrPheValG
      R   L   N   K   T   L   A   A   G   R   P   T   I   N   H   P   T   F   V   G

181  GGAGTGAACGCTGTAAACCTGGGTACACGTTCACATCTATTACCCTAAAGCCACCAAAAA   240
     lySerGluAsnCysLysProGlyTyrThrPheThrSerIleThrLeuLysProProLysI
      S   E   R   C   K   P   G   Y   T   F   T   S   I   T   L   K   P   P   K   I

241  TAGACCGTGGGTCTTATTACGGTAAAAGGTTGTTATTACCTGATTCAGTCACGGAATATG   300
     leAspArgGlySerTyrTyrGlyLysArgLeuLeuLeuProAspSerValThrGluTyrA
      D   R   G   S   Y   Y   G   K   R   L   L   L   P   D   S   V   T   E   Y   D

301  ATAAGAAGCTTGTTTCGCGCATTCAAATTCGAGTTAATCCTTTGCCGAATTTGATTCTA   360
     spLysLysLeuValSerArgIleGlnIleArgValAsnProLeuProLysPheAspSerT
      K   K   L   V   S   R   I   Q   I   R   V   N   P   L   P   K   F   D   S   T
```

FIG. 1B

```
361  CCGTGTGGGTAACAGTCCGTAAAGTTCCTGCCTCCTCGGACTTATCCGTTGCCGCCATCT  420
       hrValTrpValThrValArgLysValProAlaSerSerAspLeuSerValAlaAlaIleS
       V  W  V  T  V  R  K  V  P  A  S  S  D  L  S  V  A  A  I  S

421  CTGCTATGTTCGGGACGGAGCCTCACCGGTACTGGTTTATCAGTAGTGCTGCATCTGGAG  480
       erAlaMetPheAlaAspGlyAlaSerProValLeuValTyrGlnTyrAlaAlaSerGlyV
       A  M  F  A  D  G  A  S  P  V  L  V  Y  Q  Y  A  A  S  G  V

481  TCCAAGCTAACAACAAATTGTTGTATGATCTTTCGGCGATGCGCGCTGATATAGGTGACA  540
       alGlnAlaAsnAsnLysLeuLeuTyrAspLeuSerAlaMetArgAlaAspIleGlyAspM
       Q  A  N  N  K  L  L  Y  D  L  S  A  M  R  A  D  I  G  D  M

541  TGAGAAAGTACGCCGTCCTCGTATTCAAAAGACGATGCGCTCGAGACGGACGAGCTAG   600
       etArgLysTyrAlaValLeuValTyrSerLysAspAspAlaLeuThrAspGluLeuV
       R  K  Y  A  V  L  V  Y  S  K  D  D  A  L  E  T  D  E  L  V

601  TACTTCATGTTGACATCGAGCACCAACGTATTCCCACGTCTGGGATGCTCCCAGTCTGAT  660
       alLeuHisValAspIleGluHisGlnArgIleProThrSerGlyMetLeuProValEnd
       L  H  V  D  I  E  H  Q  R  I  P  T  S  G  M  L  P  V  *

661  TCCGTGTTCCCAGAACCCTCCCTCCGATTTCTGTGGCGGGAGCTGAGTTGGCAGTTCTGC
721  TATAAACTGTCTGAAGTCACTAAACGTTTCACGGGTTGAACGGGTTGTCCATGG   772
```

FIG. 2A

```
  1  CCATGGACAAATCTGAATCAACCAGTGCTGGTCGTAACCGTCGCGACGTCGTCCGCGTCGTG    60
     MetAspLysSerGluSerThrSerAlaGlyArgAsnArgArgArgProArgArgG
      M  D  K  S  E  S  T  S  A  G  R  N  R  R  R  R  P  R  R  G

61  GTTCCCGCTCCGCCCCCTCCTCCGCGGATGCCAACTTTAGAGTCTTGTCGCAGCAGTTT   120
     lySerArgSerAlaProSerAlaAspAlaAsnPheArgValLeuSerGlnGlnLeuS
      S  R  S  A  P  S  S  A  D  A  N  F  R  V  L  S  Q  Q  L  S

121  CGCGACTTAATAAGACGTTGTCAGCTGGTCGTCCAACTATTAACCACCCAACCTTTGTAG   180
     erArgLeuAsnLysThrLeuSerAlaGlyArgProThrIleAsnHisProThrPheValG
      R  L  N  K  T  L  S  A  G  R  P  T  I  N  H  P  T  F  V  G

181  GGAGTGAGCGTTGTAAATCTGGTACACGTTCACATCTATTACCCTAAAGCCGCCGAAAA   240
     lySerGluArgCysLysSerGlyTyrThrPheThrSerIleThrLeuLysProProLysI
      S  E  R  C  K  S  G  Y  T  F  T  S  I  T  L  K  P  P  K  I

241  TAGACCGTGGGTCTTATTATGGTAAAGGTTGTATTACCTGATTCAGTCGTCACAGAATATG   300
     leAspArgTrpValLeuLeuMetGlyLysValLeuLeuProAspSerValThrGluTyrA
      D  R  G  S  Y  Y  G  K  R  L  L  L  P  D  S  V  T  E  Y  D

301  ATAAGAAACTTGTTTCGCGCATTCAAATTCGAGTTAATCCCTTGCCCAAATTTGATTCTA   360
     spLysLysLeuValSerArgIleGlnIleArgValAsnProLeuProLysPheAspSerT
      K  K  L  V  S  R  I  Q  I  R  V  N  P  L  P  K  F  D  S  T

361  CCGTGTGGGTGACAGTCCGTAAAGTTCCTGCCTCCTCCGGACTTATCCGTTGCCGCCATCT   420
     hrValTrpValThrValArgLysValProAlaSerSerAspLeuSerValAlaAlaIleS
      V  W  V  T  V  R  K  V  P  A  S  S  D  L  S  V  A  A  I  S
```

FIG. 2B

```
421  CTGCTATGTTTGCGGACGGAGCCTCACCGGTACTGGTTTATCAGTACGCTGCATCTGGAG  480
     erAlaMetPheAlaAspGlyAlaSerProValLeuValTyrGlnTyrAlaAlaSerGlyV
      A  M  F  A  D  G  A  S  P  V  L  V  Y  Q  Y  A  A  S  G  V

481  TCCAAGCTAACAACAAATTGTTGTATGATCTTTCGGCGATGCGCGCTGATATAGGCGACA  540
     alGlnAlaAsnAsnLysLeuLeuTyrAspLeuSerAlaMetArgAlaAspIleGlyAspM
      Q  A  N  N  K  L  L  Y  D  L  S  A  M  R  A  D  I  G  D  M

541  TGAGAAAGTACGCCGTCCTCGTGTATTCAAAAGACGATGCACTCGAGACGGACGAGCTAG  600
     etArgLysTyrAlaValLeuValTyrSerLysAspAspAlaLeuGluThrAspGluLeuV
      R  K  Y  A  V  L  V  Y  S  K  D  D  A  L  E  T  D  E  L  V

601  TACTTCATGTTGACGTCGAGCACCAACGCCATTCCCACGTCTGGGGTGCTCCCAGTATAAT  660
     alLeuHisValAspValGluHisGlnArgIleProThrSerGlyValLeuProValEnd
      L  H  V  D  V  E  H  Q  R  I  P  T  S  G  V  L  P  V  *

661  TCTGTGCTTTCCAGAACCCTCCCCTCCGATTTCTGTGCGGGAGCTGAGTTGGCAGTTCTG  720
721  CTGTAAACTGTCTGAAGTCACTAAACGTTTTACGGTCAACGGGTTGTGTCCATGG      773
```

```
          RMM351                   NcoI
       5' CGTAGAATTCAGTCG......... AGCCATGGAC 3'
CMV-V27 CP ................ ..CCATGGAC AAATCTGAAT CAACCAGTGC TGGTCGTAAC CGTCGGCGTC
CMV-V33 CP ................ ..CCATGGAC AAATCTGAAT CAACCAGTGC TGGTCGTAAC CGTCGACGTC
CMV-V34 CP ................ ..CCATGGAC AAATCTGAAT CAACCAGTGC TGGTCGTAAC CGTCGACGTC
 CMV-C  CP AATTGAGTCG AGTCATGGAC AAATCTGAAT CAACCAGTGC TGGTCGTAAC CATCGACGTC
CMV-WL  CP GTCTTAGTGT GCCTATGGAC AAATCTGAT  CTCCCAATGC TAGTAGAACC TCCCGGCGTC
                                                                              420

421
CMV-V27 CP GTCCGCGTCG TGGTTCCCGC TCCGCCTCCT CCTCCTCGGA TGCTAACTTT AGAGTCTTGT
CMV-V33 CP GTCCGCGTCG TGGTTCCCGC TCCGCCCCCT CCTCCGCGGA TGCCAACTTT AGAGTCTTGT
CMV-V34 CP GTCCGCGTCG TGGTTCCCGC TCCGCCTTCCT CCTCTTCGGA TGCTAACTTT AGAGTCTTGT
 CMV-C  CP GTCCGCGTCG TGGTTCCCGC TCCGCCCCCT CCTCCGCGGA TGCTAACTTT AGAGTCTTGT
CMV-WL  CP GTCGCCCGCG TAGAGGTTCT CGGTCCGCTT CTGGTGCGGA TGCAGGGTTG CGTGCTTTGA
                                                                              480

481
CMV-V27 CP CGCAGCAGCT TTCGCGACTT AACAAGACGT TAGCAGCTGG TCGTCCAACT ATTAACCACC
CMV-V33 CP CGCAGCAGCT TTCGCGACTT AATAAGACGT TGTCAGCTGG TCGTCCAACT ATTAACCACC
CMV-V34 CP CGCAGCAGCT TTCGCGACTT AACAAGACGT TAGCAGCTGG TCGTCCAACT ATTAACCACC
 CMV-C  CP CGCAGCAGCT TTCGCGACTT AATAAGACGT TAGCAGCTGG TCGTCCAACT ATTAACCACC
CMV-WL  CP CTCAGCAGAT GCTGAAACTC AATAGAACCC TCGCCATTGG TCGTCCCACT CTTAACCACC
                                                                              540

541
CMV-V27 CP CAACCTTTGT AGGGAGTGAA CGCTGTAAAC CTGGGTACAC GTTCACATCT ATTACCCTAA
CMV-V33 CP CAACCTTTGT AGGGAGTGAG CGTTGTAAAT CTGGTACAC  GTTCACATCT ATTACCCTAA
CMV-V34 CP CAACCTTTGT AGGGAGTGAA CGCTGTAGAC CTGGGTACAC GTTCACATCT ATTACCCTAA
 CMV-C  CP CAACCTTTGT AGGGAGTGAA CGCTGTAGAC CTGGGTACAC GTTCACATCT ATTACCCTAA
CMV-WL  CP CAACCTTCGT GGGTAGTGAA AGCTGTAAAC CCGGTTACAC TTTCACATCT ATTACCCTGA
                                                                              600
```

FIG. 4B

```
           601
CMV-V27 CP AGCCACCAAA AATAGACCGT GGGTCTTATT ACGGTAAAAG GTTGTTATTA CCTGATTCAG
CMV-V33 CP AGCCGCCGAA AATAGACCGT GGGTCTTATT ATGGTAAAAG GTTGTTATTA CCTGATTCAG
CMV-V34 CP AGCCACCAAA AATAGACCGC GGGTCTTACT ACGGTAAAAG GTTGTTACTA CCTGATTCAG
 CMV-C  CP AGCCACCAAA AATAGACCGT GAGTCTTATT ACGGTAAAAG GTTGTTACTA CCTGATTCAG
 CMV-WL CP AACCGCCTGA AATTGAGAAA GGTTCATATT TTGGTAGAAG GTTGTCTTTG CCAGATTCAG 661                                                         720
CMV-V27 CP TCACGGAATA TGATAAGAAG CTTGTTTTCGC GCATTCAAAT TCGAGTTAAT CCTTTGCCGA
CMV-V33 CP TCACAGAATA TGATAAGAAA CTTGTTTTCGC GCATTCAAAT TCGAGTTAAT CCCTTGCCGA
CMV-V34 CP TCACGGAATA TGATAAGAAG CTTGTTTTCGC GCATTCAAAT TCGAGTTAAT CCTTTGCCGA
 CMV-C  CP TCACGGAATA TGATAAGAAG CTTGTTTTCGC GCATTCAAAT TCGAGTTAAT CCTTTGCCGA
 CMV-WL CP TCACGGACTA TGATAAGAAG CTTGTTTTCGC GCATTCAAAT CAGGGTTAAT CCTTTGCCGA 721                                                         780
CMV-V27 CP AATTTGATTC TACCGTGTGG GTAACAGTCC GTAAAGTTCC TGCCTCCTCG GACTTATCCG
CMV-V33 CP AATTTGATTC TACCGTGTGG GTGACAGTCC GTAAAGTTCC TGCCTCCTCG GACTTATCCG
CMV-V34 CP AATTTGATTC TACCGTGTGG GTGACAGTTC GTAAAGTTCC TGCCTCCTCG GACTTATCCG
 CMV-C  CP AATTTGATTC TACCGTGTGG GTGACAGTCC GTAAAGTTCC TGCCTCCTCG GACTTATCCG
 CMV-WL CP AATTTGATTC TACCGTGTGG GTTACAGTTC GGAAAGTACC TTCATCATCC GATCTTTCCG 781                                                         840
CMV-V27 CP TTGCCGCCAT CTCTGCTATG TTCGCGGACG GAGCCTCACC GGTACTGGTT TATCAGTATG
CMV-V33 CP TTGCCGCCAT CTCTGCTATG TTTGCGGACG GAGCCTCACC GGTACTGGTT TATCAGTACG
CMV-V34 CP TTGCCGCCAT CTCTGCTATG TTCGCGGACG GAGCCTCACC GGTACTGGTT TATCAGTATG
 CMV-C  CP TTGCCGCCAT CTCTGCTATG TTCGCGGACG GAGCCTCACC GGTACTGGTT TATCAGTATG
 CMV-WL CP TCGCCGCCAT CTCTGCTATG TTTGGCGATG GTAATTCACC GGTTTTGGTT TATCAGTATG
```

FIG. 4C

```
          841
CMV-V27 CP  CTGCATCTGG AGTCCAAGCT AACAACAAAT TGTTGTATGA TCTTTCGGCG ATGCGCGCTG  900
CMV-V33 CP  CTGCATCTGG AGTCCAAGCT AACAACAAAT TGTTGTATGA TCTTTCGGCG ATGCGCGCTG
CMV-V34 CP  CTGCATCTGG AGTTCAAGCT AACAACAAAT TGTTGTATGA TCTTTCGGCG ATGCGCGCTG
CMV-C   CP  CCGCATCTGG AGTCCAAGCC AACAACAAAC TGTTGTTTGA TCTTTCGGCG ATGCGCGCTG
CMV-WL  CP  CTGCGTCCGG AGTTCAGGCC AACAATAAGT TACTTTATGA CCTGTCCGAG ATGCGTGCTG

901
CMV-V27 CP  ATATAGGTGA CATGAGAAAG TACGCCGTCC TCGTGTATTC AAAAGACGAT GCGCTCGAGA  960
CMV-V33 CP  ATATAGCCGA CATGAGAAAG TACGCCGTCC TCGTGTATTC AAAAGACGAT GCACTCGAGA
CMV-V34 CP  ATATAGGTGA CATGAGAAAG TACGCCGTCC TCGTGTATTC AAAAGACGAT GCACTCGAGA
CMV-C   CP  ATATAGGTGA CATGAGAAAG TACGCCGTCC TCGTGTATTC AAAAGACGAT GCGCTCGAGA
CMV-WL  CP  ATATCGGCGA CATGCGTAAG TACGCCGTCC TGGTTTACTC GAAAGACGAT AAACTAGAGA

961
CMV-V27 CP  CGGACGAGCT AGTACTTCAT GTTGACATCG AGCACCAACG TATTCCCACG TCTGGGATGC  1020
CMV-V33 CP  CGGACGAGCT AGTACTTCAT GTTGACGTCG AGCACCAACG CATTCCCACG TCTGGGGTGC
CMV-V34 CP  CGGACGAGCT AGTACTTCAT GTTGACATCG AGCACCAACG CATTCCCACG TCTGGGGTGC
CMV-C   CP  CGGACGAGCT AGTACTTCAT GTTGACATCG AGCACCAACA CATTCCCACG TCTGGAGTGC
CMV-WL  CP  AGGACGAGAT TGCACTTCAT GTCGACGTCG AGCACCAACG AATTCCTATC TCACGGATGC

1021
CMV-V27 CP  TCC........ ..CAGTCTGA TTCCGTG.TT CCCAGAACCC T.CCCTCCGA TTTCTGTGGC  1080
CMV-V33 CP  TCC........ ..CAGTATAA TTCTGTGCTT TCCAGAACCC T.CCCTCCGA TTTCTGTGGC
CMV-V34 CP  TCC........ ..CAGTTTGA TTCCGTG.TT .CCAGAACCC T.CCCTCCGA TTTCTGTGGC
CMV-C   CP  TCC........ ..CAGTCTGA TTCCGTG.TT CCCAGAACCC T.CCCTCCGA TCTCTGTGGC
CMV-WL  CP  TCCCGACTTA GTCCGTGTGT TTACGGGCGT CCGAGAACGT TAAACTACAC TCTCAATCGC
```

FIG. 4D

```
            1081
CMV-V27 CP  GGGAGCTGAG TTGGCAGTTC TGCTATAAAC TGTCTCTGAAGT CACTAAAACGT          1140
CMV-V33 CP  GGGAGCTGAG TTGGCAGTTC TGCTGTAAAC TGTCTCTGAAGT CACTAAAACGT  ....TTCACG
CMV-V34 CP  GGGAGCTGAG TTGGCAGTTC TGCTATAAAC TGTCTCTGAAGT CACTAAAACGT  ....TTTACG
CMV-C   CP  GGGAGCTGAG TTGGCAGTTC TACTACAAAC TGTCTCTGAAGT CACTAAAACGT  ....TTTACG
CMV-WL  CP  GAGTGCTGAC TTGGTAGTAT TGCTTCAAAC TGCCTGAAGT  CCCTAAAACGT  ....TTTACG
                                                                    GTTGTTGCGC

1141
CMV-V27 CP  GTGAACGGGT TGTCCATGG                                              1200
CMV-V33 CP  GTGAACGGGT TGTCCATGG
CMV-V34 CP  GTGAACGGGT TGTCCATGG
CMV-C   CP  GTGAACGGGT TGTCCATCCA GCTTACGGCT
CMV-WL  CP  GGGGAACGGG TGTCCATCCA GCTTACGGCT
RMM352-->3' CAGGTACCT CGAATGCCGAGCTCACCAG 5'
            Nco I
```

FIG. 5A

```
                                                                                          *50
CMV-V34 CP     1 MDKSESTSAG R.NRRRRPRR GSRSASSSSD ANFRVLSQQL SRLNKTLAAG
CMV-V27 CP       MDKSESTSAG R.NRRRRPRR GSRSASSSSD ANFRVLSQQL SRLNKTLAAG
CMV-C   CP       MDKSESTSAG R.NHRRRPRR GSRSAPSSAD ANFRVLSQQL SRLNKTLAAG
CMV-V33 CP       MDKSESTSAG R.NRRRRPRR GSRSAPSSAD ANFRVLSQQL SRLNKTLSAG
CMV-Q3  CP       MDKSGSPNAS RTSRRRRPRR GSRSA.SGAD AGLRALTQQM LRLNKTLAIG
CMV-WL  CP       MDKSGSPNAS RTSRRRRPRR GSRSA.SGAD AGLRALTQQM LKLNRTLAIG

*                                              100
CMV-V34 CP    51 RPTINHPTFV GSERCRPGYT FTSITLKPPK IDRGSYYGKR LLLPDSVTEY
CMV-V27 CP       RPTINHPTFV GSERCKPGYT FTSITLKPPK IDRGSYYGKR LLLPDSVTEY
CMV-C   CP       RPTINHPTFV GSERCRPGYT FTSITLKPPK IDRESYYGKR LLLPDSVTEY
CMV-V33 CP       RPTINHPTFV GSERCKPGYT FTSITLKPPK IDRGSYYGKR LLLPDSVTEY
CMV-Q3  CP       RPTLNHPTFV GSESCKPGYT FTSITLKPPE IEKGSYFGRR LSLPDSVTDY
CMV-WL  CP       RPTLNHPTFV GSESCKPGYT FTSITLKPPE IEKGSYFGRR LSLPDSVTDY

150
CMV-V34 CP   101 DKKLVSRIQI RVNPLPKFDS TVWVTVRKVP ASSDLSVAAI SAMFADGASP
CMV-V27 CP       DKKLVSRIQI RVNPLPKFDS TVWVTVRKVP ASSDLSVAAI SAMFADGASP
CMV-C   CP       DKKLVSRIQI RVNPLPKFDS TVWVTVRKVP ASSDLSVAAI SAMFADGASP
CMV-V33 CP       DKKLVSRIQI RVNPLPKFDS TVWVTVRKVP ASSDLSVAAI SAMFADGASP
CMV-Q3  CP       DKKLVSRIQI RVNPLPKFDS TVWVTVRKVP SSSDLSVAAI SAMFGDGNSP
CMV-WL  CP       DKKLVSRIQI RVNPLPKFDS TVWVTVRKVP SSSDLSVAAI SAMFGDGNSP
```

FIG. 5B

```
          151                                                              200
CMV-V34 CP  VLVYQYAASG VQANNKLLYD LSAMRADIGD MRKYAVLVYS KDDALETDEL
CMV-V27 CP  VLVYQYAASG VQANNKLLYD LSAMRADIGD MRKYAVLVYS KDDALETDEL
CMV-C   CP  VLVYQYAASG VQANNKLLYD LSAMRADIGD MRKYAVLVYS KDDALETDEL
CMV-V33 CP  VLVYQYAASG VQANNKLLYD LSAMRADIGD MRKYAVLVYS KDDALETDEL
CMV-Q3  CP  VLVYQYAASG VQANNKLLYD LSEMRADIGD MRKYAVLVYS KDDKLEKDEI
CMV-WL  CP  VLVYQYAASG VQANNKLLYD LSEMRADIGD MRKYAVLVYS KDDKLEKDEI

201        *                                                    250
CMV-V34 CP  VLHVDIEHQR IPTSGVLPV*
CMV-V27 CP  VLHVDIEHQR IPTSGMLPV*
CMV-C   CP  VLHVDIEHQR IPTSGVLPV*
CMV-V33 CP  VLHVDVEHQR IPTSGVLPV*
CMV-Q3  CP  VLHVDVEHQR IPISRMLPT*
CMV-WL  CP  ALHVDVEHQR IPISRMLPT*
```

FIG. 8

```
CCATGGACAAATCTGAATCAACCAGTGCTGGTCGTGACGTCGTCCGCGTCGTG    60
  M   D   K   S   E   S   T   S   A   G   R   N   R   R   R   P   R   R   G
GTTCCCGCTCCGCCCCTCTCCCGCGGATGCTAACTTTAGAGTCCTGTCGCAGCAGCTTT   120
  S   R   S   A . L   S   S   A   D   A   N   F   R   V   L   S   Q   Q   L   S
CGCGACTTAATAAGACGTTAGCAGTCTGGTCGTCCAACTATTAACCACCAACCTTTGTAG   180
  R   L   N   K   T   L   A   A   G   R   P   T   I   N   H   P   T   F   V   G
GGAGTGAACGCTGTAGACCTGGGTACACGTTCACATCTATTACCCTAAAGCCACCAAAAA   240
  S   E   R   C   R   P   G   Y   T   F   T   S   I   T   L   K   P   P   K   I
TAGACCGTGGGTCTTATTACGGTAAAAGTTGTTACTACCTGATTCAGTCACAGAATATG   300
  D   R   G   S   Y   Y   G   K   R   L   L   L   P   D   S   V   T   E   Y   D
ATAAGAAGCTTGTTTCGCGCATTCAAATTCGAGTTAATCCTTTGCCGAAATTTGATTCTA   360
  K   K   L   V   S   R   I   Q   I   R   V   N   P   L   P   K   F   D   S   T
CCGTGTGGGTGACAGTCCGTAAAGTTCCTGCCTCCTCCGGACTTATCCGTTGCCGCCATCT   420
  V   W   V   T   V   R   K   V   P   A   S   S   D   L   S   V   A   A   I   S
CTGCTATGTTCGCGGACGGAGCCTCACCGTACTGGTTTATCAGTATGCCGATCTGGAG   480
  A   M   F   A   D   G   A   S   P   V   L   V   Y   Q   Y   A   A   S   G   V
TCCAAGCCAACAACAAACTGTTGTATGATCTTTCGGCGATGCGCGCTGATATAGGTGACA   540
  Q   A   N   N   K   L   L   Y   D   L   S   A   M   R   A   D   I   G   D   M
TGAGAAAGTACGCCGTCCTCGTGTATTCAAAAGACGATGCTCTGGAGTGCTCCCAGTCTGAT   600
  R   K   Y   A   V   L   V   Y   S   K   D   D   A   L   E   T   D   E   L   V
TACTTCATGTTGACATCGAGCACCACAGCATTCCCACGTCTGGAGTTGGCAGTTCTGC   660
  L   H   V   D   I   E   H   Q   R   I   P   T   S   G   V   L   P   V . F
TCTGTGTTCCCAGAACCCCTCCCGATCTCTGTGGCGGAGCTGAGTTGGCAGTTCTGC   720
  C   V   P   R   T   L   P   P   I   S   V   A   G   A   E   L   A   V   L
TGTAAACTGTCTGAAGTCACTAAACGTTTTACGGTGAACGGGTTGTCTTGCCATGG     772
      T V . S   H .   T   F   Y   G   E   R   V   V   H   G
```

FIG. 9A

|   | Majority | |
|---|---|---|
| MDKSESTSAGR-NRRRRPRRGSRSASSSADANFRVLSQQL | | |
| | 10 | 20 | 30 | 40 |

| Sequence | Residues 1–40 | Label |
|---|---|---|
| 1 | MDKSESTSAGRR-RRRPRRGSRSASSSADANFRVLSQQL | CMV-C CP AA SEQ |
| 1 | MDKSESTSAGRR-RRRPRRGSRSALSSADANFRVLSQQL | CMV-A35 CP AA SEQ |
| 1 | MDKSESTSAGRR-RRRPRRGSRSA[P]SSADANFRVLSQQL | CMV-V27 CP AA SEQ |
| 1 | MDKSESTSAGRR-

FIG. 9B

| | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|
| | T | V | W | T | V | R | K | V | P | A | S | S | D | L | S | V | A | A | I | S | A | M | F | A | D | G | A | S | P | V | L | V | Y | Q | Y | A | A | S | G | Majority |
| | | | | | | | | | | 130 | | | | | | | 140 | | | | | | | | | | 150 | | | | | | | | | 160 | | | | |
| 120 | T | V | W | V | T | V | R | K | V | P | A | S | S | D | L | S | V | A | A | I | S | A | M | F | A | D | G | A | S | P | V | L | V | Y | Q | Y | A | A | S | G | CMV-C CP AA SEQ |
| 120 | T | V | V | V | T | V | R | K | V | P | A | S | S | D | L | S | V | A | A | I | S | A | M | F | A | D | G | A | S | P | V | L | V | Y | Q | Y | A | A | S | G | CMV-A35 CP AA SEQ |
| 120 | T | V | V | V | T | V | R | R | K | V | P | A | S | S | D | L | S | V | A | A | I | S | A | M | F | A | D | G | A | S | P | V | L | V | Y | Q | Y | A | A | S | G | CMV-V27 CP AA SEQ |
| 120 | T | V | V | V | T | V | R | K | V | P | A | S | S | D | L | S | V | A | A | I | S | A | M | F | A | D | G | A | S | P | V | L | V | Y | Y | Q | Y | A | A | S | G | CMV-V33 CP AA SEQ |
| 120 | T | V | V | V | T | V | R | K | V | P | A | S | S | D | L | S | V | A | A | I | S | A | M | F | A | D | G | A | S | P | V | L | V | Y | Q | Y | A | A | S | G | CMV-V34 CP AA SEQ |
| 120 | T | V | W | V | T | V | R | K | V | P | [S] | S | D | L | S | V | A | A | I | S | A | M | F | A | D | [G] | [N] | S | P | V | L | V | Y | Q | Y | A | A | S | G | | CMV-WL CP AA SEQ |

| | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|
| | V | Q | A | N | N | K | L | L | Y | D | L | S | A | M | R | A | D | I | G | D | M | R | K | Y | A | V | L | V | Y | S | K | D | D | A | L | E | T | D | E | L | Majority |
| | | | | | | | | | | 170 | | | | | | | 180 | | | | | | | | | | 190 | | | | | | | | | 200 | | | | |
| 160 | V | Q | A | N | N | K | L | L | Y | D | L | S | A | M | R | A | D | I | G | D | M | R | K | Y | A | V | L | V | Y | S | K | D | D | A | L | E | T | D | E | L | CMV-C CP AA SEQ |
| 160 | V | Q | A | N | N | K | L | L | Y | D | L | S | A | M | R | A | D | I | G | D | M | R | K | Y | A | V | L | V | Y | S | K | D | D | A | L | E | T | D | E | L | CMV-A35 CP AA SEQ |
| 160 | V | Q | A | N | N | K | L | L | Y | D | L | S | A | M | R | A | D | I | G | D | M | R | K | Y | A | V | L | V | Y | S | K | D | D | A | L | E | T | D | E | L | CMV-V27 CP AA SEQ |
| 160 | V | Q | A | N | N | K | L | L | Y | D | L | S | A | M | R | A | D | I | G | D | M | R | K | Y | A | V | L | V | Y | S | K | D | D | A | L | E | T | D | E | L | CMV-V33 CP AA SEQ |
| 160 | V | Q | A | N | N | K | L | L | Y | D | L | S | A | M | R | A | D | I | G | D | M | R | K | Y | A | V | L | V | Y | S | K | D | D | A | L | E | T | D | E | L | CMV-V34 CP AA SEQ |
| 160 | V | Q | A | N | N | K | L | [F] | Y | D | L | S | [E] | M | R | A | D | I | G | D | M | R | K | Y | A | V | L | V | Y | S | K | D | D | [K] | L | E | [K] | D | E | [I] | CMV-WL CP AA SEQ |

| | | | | | | | | | | | | | | | | | | | | | |
|---|---|---|---|---|---|---|---|---|---|---|---|---|---|---|---|---|---|---|---|---|---|
| | V | L | H | V | D | I | E | H | Q | R | I | P | T | S | G | V | L | P | V | - | Majority |
| | | | | | | | | | | 210 | | | | | | | 220 | | | | |
| 200 | V | L | H | V | D | D | I | E | H | Q | R | I | P | T | S | G | V | L | P | V | . | CMV-C CP AA SEQ |
| 200 | V | L | H | V | D | D | I | E | H | Q | R | I | P | T | S | G | V | L | P | V | . | CMV-A35 CP AA SEQ |
| 200 | V | L | H | V | D | [V] | I | E | H | Q | R | I | P | T | S | G | [M] | L | P | V | . | CMV-V27 CP AA SEQ |
| 200 | V | L | H | V | D | D | I | E | H | Q | R | I | P | T | S | G | V | L | P | V | . | CMV-V33 CP AA SEQ |
| 200 | V | L | H | V | D | [V] | I | E | H | Q | R | I | P | T | S | G | V | L | P | V | . | CMV-V34 CP AA SEQ |
| 200 | [A] | L | H | V | D | D | I | E | H | Q | R | I | P | S | [R] | [M] | L | P | [T] | . | | CMV-WL CP AA SEQ |

FIG. 10A

```
          X X X X X X X X X X X X X X X X X X X X    Majority
                     330                 340
    1     . . . . . . . . . . . . . . . . . . . .    CMV-A35 CP
   321    T A G A G A G T G T G T G T G C T G T G    CMV-C CP
    1     . . . . . . . . . . . . . . . . . . . .    CMV-V34 CP
   247    . . . . . . . . . T G A G T C G T G T G    CMV-WL CP
    1     . . . . . . . . . . . . . . . . . . . .    CMV-V27 CP
    1     . . . . . . . . . . . . . . . . . . . .    CMV-V33 CP X X X X X X X X X X X X X X X X X X X X    Majority
                     350                 360
    1     . . . . . . . . . . . . . . . . . . . .    CMV-A35 CP
   341    T T T T C T C T T T T G T G T C G T A G    CMV-C CP
    1     . . . . . . . . . . . . . . . . . . . .    CMV-V34 CP
   258    T T T T G T A T T T T G C G T C T T A G    CMV-WL CP
    1     . . . . . . . . . . . . . . . . . . . .    CMV-V27 CP
    1     . . . . . . . . . . . . . . . . . . . .    CMV-V33 CP X X X X X X X X X X X C C A T G G A C      Majority
                     370                 380
    1     . . . . . . . . . . . C C A T G G A C      CMV-A35 CP
   361    A A T T G A G T C G A G T C A T G G A C    CMV-C CP
    1     . . . . . . . . . . . C C A T G G A C      CMV-V34 CP
   278    . . . T G T G C . . . C T A T G G A C      CMV-WL CP
    1     . . . . . . . . . . . C C A T G G A C      CMV-V27 CP
    1     . . . . . . . . . . . C C A T G G A C      CMV-V33 CP A A A T C T G A A T C A A C C A G T G C    Majority
                     390                 400
    9     A A A T C T G A A T C A A C C A G T G C    CMV-A35 CP
   381    A A A T C T G A A T C A A C C A G T G C    CMV-C CP
    9     A A A T C T G A A T C A A C C A G T G C    CMV-V34 CP
   291    A A A T C T G A T C T C C C A A T G C      CMV-WL CP
    9     A A A T C T G A A T C A A C C A G T G C    CMV-V27 CP
    9     A A A T C T G A A T C A A C C A G T G C    CMV-V33 CP
```

FIG. 10B

```
         T G G T C G T A A C C G T C G A C G T C   Majority
                         410                 420
  29     T G G T C G T A A C C G T C G A C G T C   CMV-A35 CP
 401     T G G T C G T A A C C A T C G A C G T C   CMV-C   CP
  29     T G G T C G T A A C C G T C G A C G T C   CMV-V34 CP
 311     T A G T A G A A C C T C C C G G C G T C   CMV-WL  CP
  29     T G G T C G T A A C C G T C G G C G T C   CMV-V27 CP
  29     T G G T C G T A A C C G T C G A C G T C   CMV-V33 CP G T C X X X C G C G T C G T G G T T C C   Majority
                         430                 440
  49     G T C . . . C G C G T C G T G G T T C C   CMV-A35 CP
 421     G T C . . . C G C G T C G T G G T T C C   CMV-C   CP
  49     G T C . . . C G C G T C G T G G T T C C   CMV-V34 CP
 331     G T C G C C C G C G T A G A G G T T C T   CMV-WL  CP
  49     G T C . . . C G C G T C G T G G T T C C   CMV-V27 CP
  49     G T C . . . C G C G T C G T G G T T C C   CMV-V33 CP C G C T C C G C C C C C T C C T C C G C   Majority
                         450                 460
  66     C G C T C C G C C C T C T C C T C C G C   CMV-A35 CP
 438     C G C T C C G C C C C C T C C T C C G C   CMV-C   CP
  66     C G C T C C G C T T C C T C C T C T T C   CMV-V34 CP
 351     C G G T C C G C T . . . T C T G G T G C   CMV-WL  CP
  66     C G C T C C G C C T C T T C C T C C T C   CMV-V27 CP
  66     C G C T C C G C C C C C T C C T C C G C   CMV-V33 CP G G A T G C T A A C T T T A G A G T C T   Majority
                         470                 480
  86     G G A T G C T A A C T T T A G A G T C C   CMV-A35 CP
 458     G G A T G C T A A C T T T A G A G T C T   CMV-C   CP
  86     G G A T G C T A A C T T T A G A G T C T   CMV-V34 CP
 368     G G A T G C A G G G T T G C G T G C T T   CMV-WL  CP
  86     G G A T G C T A A C T T T A G A G T C T   CMV-V27 CP
  86     G G A T G C C A A C T T T A G A G T C T   CMV-V33 CP
```

FIG. 10C

```
    T G T C G C A G C A G C T T T C G C G A   Majority
                    490              500
106 T G T C G C A G C A G C T T T C G C G A   CMV-A35 CP
478 T G T C G C A G C A G C T T T C G C G A   CMV-C CP
106 T G T C G C A G C A G C T T T C G C G A   CMV-V34 CP
388 T G A C T C A G C A G A T G C T G A A A   CMV-WL CP
106 T G T C G C A G C A G C T T T C G C G A   CMV-V27 CP
106 T G T C G C A G C A G C T T T C G C G A   CMV-V33 CP C T T A A T A A G A C G T T A G C A G C   Majority
                    510              520
126 C T T A A T A A G A C G T T A G C A G C   CMV-A35 CP
498 C T T A A T A A G A C G T T A G C A G C   CMV-C CP
126 C T T A A C A A G A C G T T A G C A G C   CMV-V34 CP
408 C T C A A T A G A A C C C T C G C C A T   CMV-WL CP
126 C T T A A C A A G A C G T T A G C A G C   CMV-V27 CP
126 C T T A A T A A G A C G T T G T C A G C   CMV-V33 CP T G G T C G T C C A A C T A T T A A C C   Majority
                    530              540
146 T G G T C G T C C A A C T A T T A A C C   CMV-A35 CP
518 T G G T C G T C C A A C T A T T A A C C   CMV-C CP
146 T G G T C G T C C A A C T A T T A A C C   CMV-V34 CP
428 T G G T C G T C C C A C T C T T A A C C   CMV-WL CP
146 T G G T C G T C C A A C T A T T A A C C   CMV-V27 CP
146 T G G T C G T C C A A C T A T T A A C C   CMV-V33 CP A C C C A A C C T T T G T A G G G A G T   Majority
                    550              560
166 A C C C A A C C T T T G T A G G G A G T   CMV-A35 CP
538 A C C C A A C C T T T G T A G G G A G T   CMV-C CP
166 A C C C A A C C T T T G T A G G G A G T   CMV-V34 CP
448 A C C C A A C C T T C G T G G G T A G T   CMV-WL CP
166 A C C C A A C C T T T G T A G G G A G T   CMV-V27 CP
166 A C C C A A C C T T T G T A G G G A G T   CMV-V33 CP
```

FIG. 10D

```
       G A A C G C T G T A G A C C T G G G T A   Majority
                       570                 580
186    G A A C G C T G T A G A C C T G G G T A   CMV-A35 CP
558    G A A C G C T G T A G A C C T G G G T A   CMV-C CP
186    G A A C G C T G T A G A C C T G G G T A   CMV-V34 CP
468    G A A A G C T G T A A A C C C G G T T A   CMV-WL CP
186    G A A C G C T G T A A A C C T G G G T A   CMV-V27 CP
186    G A G C G T T G T A A A T C T G G G T A   CMV-V33 CP C A C G T T C A C A T C T A T T A C C C   Majority
                       590                 600
206    C A C G T T C A C A T C T A T T A C C C   CMV-A35 CP
578    C A C G T T C A C A T C T A T T A C C C   CMV-C CP
206    C A C G T T C A C A T C T A T T A C C C   CMV-V34 CP
488    C A C T T T C A C A T C T A T T A C C C   CMV-WL CP
206    C A C G T T C A C A T C T A T T A C C C   CMV-V27 CP
206    C A C G T T C A C A T C T A T T A C C C   CMV-V33 CP T A A A G C C A C C A A A A A T A G A C   Majority
                       610                 620
226    T A A A G C C A C C A A A A A T A G A C   CMV-A35 CP
598    T A A A G C C A C C A A A A A T A G A C   CMV-C CP
226    T A A A G C C A C C A A A A A T A G A C   CMV-V34 CP
508    T G A A A C C G C C T G A A A T T G A G   CMV-WL CP
226    T A A A G C C A C C A A A A A T A G A C   CMV-V27 CP
226    T A A A G C C G C C G A A A A T A G A C   CMV-V33 CP C G T G G G T C T T A T T A C G G T A A   Majority
                       630                 640
246    C G T G G G T C T T A T T A C G G T A A   CMV-A35 CP
618    C G T G A G T C T T A T T A C G G T A A   CMV-C CP
246    C G C G G G T C T T A C T A C G G T A A   CMV-V34 CP
528    A A A G G T T C A T A T T T T G G T A G   CMV-WL CP
246    C G T G G G T C T T A T T A C G G T A A   CMV-V27 CP
246    C G T G G G T C T T A T T A T G G T A A   CMV-V33 CP
```

FIG. 10E

```
        A A G G T T G T T A T T A C C T G A T T    Majority
                        650                660
266     A A G G T T G T T A C T A C C T G A T T    CMV-A35 CP
638     A A G G T T G T T A C T A C C T G A T T    CMV-C CP
266     A A G G T T G T T A C T A C C T G A T T    CMV-V34 CP
548     A A G G T T G T C T T T G C C A G A T T    CMV-WL CP
266     A A G G T T G T T A T T A C C T G A T T    CMV-V27 CP
266     A A G G T T G T T A T T A C C T G A T T    CMV-V33 CP C A G T C A C G G A A T A T G A T A A G    Majority
                        670                680
286     C A G T C A C A G A A T A T G A T A A G    CMV-A35 CP
568     C A G T C A C G G A A T A T G A T A A G    CMV-C CP
286     C A G T C A C G G A A T A T G A T A A G    CMV-V34 CP
568     C A G T C A C G G A C T A T G A T A A G    CMV-WL CP
286     C A G T C A C G G A A T A T G A T A A G    CMV-V27 CP
286     C A G T C A C A G A A T A T G A T A A G    CMV-V33 CP A A G C T T G T T T C G C G C A T T C A    Majority
                        690                700
306     A A G C T T G T T T C G C G C A T T C A    CMV-A35 CP
678     A A G C T T G T T T C G C G C A T T C A    CMV-C CP
306     A A G C T T G T T T C G C G C A T T C A    CMV-V34 CP
588     A A G C T T G T T T C G C G C A T T C A    CMV-WL CP
306     A A G C T T G T T T C G C G C A T T C A    CMV-V27 CP
306     A A A C T T G T T T C G C G C A T T C A    CMV-V33 CP A A T T C G A G T T A A T C C T T T G C    Majority
                        710                720
326     A A T T C G A G T T A A T C C T T T G C    CMV-A35 CP
698     A A T T C G A G T T A A T C C T T T G C    CMV-C CP
326     A A T T C G A G T T A A T C C T T T G C    CMV-V34 CP
608     A A T C A G G G T T A A T C C T T T G C    CMV-WL CP
326     A A T T C G A G T T A A T C C T T T G C    CMV-V27 CP
326     A A T T C G A G T T A A T C C C T T G C    CMV-V33 CP
```

FIG. 10F

```
      C G A A A T T T G A T T C T A C C G T G    Majority
                        730                 740
346  | C G A A A T T T G A T T C T A C C G T G |  CMV-A35 CP
718  | C G A A A T T T G A T T C T A C C G T G |  CMV-C CP
346  | C G A A A T T T G A T T C T A C C G T G |  CMV-V34 CP
628  | C G A A A T T T G A T T C T A C C G T G |  CMV-WL CP
346  | C G A A A T T T G A T T C T A C C G T G |  CMV-V27 CP
346  | C G A A A T T T G A T T C T A C C G T G |  CMV-V33 CP T G G G T G A C A G T C C G T A A A G T    Majority
                        750                 760
266  | T G G G T G A C A G T C C G T A A A G T |  CMV-A35 CP
738  | T G G G T G A C A G T C C G T A A A G T |  CMV-C CP
366  | T G G G T G A C A G T[T]C G T A A A G T |  CMV-V34 CP
648  | T G G G T[T]A C A G T[T]C G[G]A A A G T |  CMV-WL CP
366  | T G G G T[A]A C A G T C C G T A A A G T |  CMV-V27 CP
366  | T G G G T G A C A G T C C G T A A A G T |  CMV-V33 CP T C C T G C C T C C T C G G A C T T A T    Majority
                        770                 780
386  | T C C T G C C T C C T C G G A C T T A T |  CMV-A35 CP
758  | T C C T G C C T C C T C G G A C T T A T |  CMV-C CP
386  | T C C T G C C T C C T C G G A C T T A T |  CMV-V34 CP
668  |[A]C C T[T]C[A]T C[A]T C[C]G A[T C]T[T]T |  CMV-WL CP
386  | T C C T G C C T C C T C G G A C T T A T |  CMV-V27 CP
386  | T C C T G C C T C C T C G G A C T T A T |  CMV-V33 CP C C G T T G C C G C C A T C T C T G C T    Majority
                        790                 800
406  | C C G T T G C C G C C A T C T C T G C T |  CMV-A35 CP
778  | C C G T T G C C G C C A T C T C T G C T |  CMV-C CP
406  | C C G T T G C C G C C A T C T C T G C T |  CMV-V34 CP
688  | C C G T[C]G C C G C C A T C T C T G C T |  CMV-WL CP
406  | C C G T T G C C G C C A T C T C T G C T |  CMV-V27 CP
406  | C C G T T G C C G C C A T C T C T G C T |  CMV-V33 CP
```

FIG. 10G

```
        A T G T T C G C G G A C G G A G C C T C   Majority
                      810                 820
426     A T G T T C G C G G A C G G A G C C T C   CMV-A35 CP
798     A T G T T C G C G G A C G G A G C C T C   CMV-C CP
426     A T G T T C G C G G A C G G A G C C T C   CMV-V34 CP
708     A T G T T T G C G A T G G T A A T T C     CMV-WL CP
426     A T G T T C G C G G A C G G A G C C T C   CMV-V27 CP
426     A T G T T T G C G G A C G G A G C C T C   CMV-V33 CP A C C G G T A C T G G T T T A T C A G T   Majority
                      830                 840
446     A C C G G T A C T G G T T T A T C A G T   CMV-A35 CP
818     A C C G G T A C T G G T T T A T C A G T   CMV-C CP
446     A C C G G T A C T G G T T T A T C A G T   CMV-V34 CP
728     A C C G G T T T T G G T T T A T C A G T   CMV-WL CP
446     A C C G G T A C T G G T T T A T C A G T   CMV-V27 CP
446     A C C G G T A C T G G T T T A T C A G T   CMV-V33 CP A T G C T G C A T C T G G A G T C C A A   Majority
                      850                 860
466     A T G C C G C A T C T G G A G T C C A A   CMV-A35 CP
838     A T G C C G C A T C T G G A G T C C A A   CMV-C CP
466     A T G C T G C A T C T G G A G T T C A A   CMV-V34 CP
748     A T G C T G C G T C C G G A G T T C A G   CMV-WL CP
466     A T G C T G C A T C T G G A G T C C A A   CMV-V27 CP
466     A C G C T G C A T C T G G A G T C C A A   CMV-V33 CP G C T A A C A A C A A A T T G T T G T A   Majority
                      870                 880
486     G C C A A C A A C A A A C T G T T G T A   CMV-A35 CP
858     G C C A A C A A C A A A C T G T T G T T   CMV-C CP
486     G C T A A C A A C A A A T T G T T G T A   CMV-V34 CP
768     G C C A A C A A T A A G T T A C T T T A   CMV-WL CP
486     G C T A A C A A C A A A T T G T T G T A   CMV-V27 CP
486     G C T A A C A A C A A A T T G T T G T A   CMV-V33 CP
```

FIG. 10H

```
        T G A T C T T T C G G C G A T G C G C G    Majority
                      890                 900
   506  T G A T C T T T C G G C G A T G C G C G    CMV-A35 CP
   878  T G A T C T T T C G G C G A T G C G C G    CMV-C CP
   506  T G A T C T T T C G G C G A T G C G C G    CMV-V34 CP
   788  T G A C C T G T C C G A G A T G C G T G    CMV-WL CP
   506  T G A T C T T T C G G C G A T G C G C G    CMV-V27 CP
   506  T G A T C T T T C G G C G A T G C G C G    CMV-V33 CP C T G A T A T A G G T G A C A T G A G A    Majority
                      910                 920
   526  C T G A T A T A G G T G A C A T G A G A    CMV-A35 CP
   898  C T G A T A T A G G T G A C A T G A G A    CMV-C CP
   526  C T G A T A T A G G T G A C A T G A G A    CMV-V34 CP
   808  C T G A T A T C G G C G A C A T G C G T    CMV-WL CP
   526  C T G A T A T A G G T G A C A T G A G A    CMV-V27 CP
   526  C T G A T A T A G G C G A C A T G A G A    CMV-V33 CP A A G T A C G C C G T C C T C G T G T A    Majority
                      930                 940
   546  A A G T A C G C C G T C C T C G T G T A    CMV-A35 CP
   918  A A G T A C G C C G T C C T C G T G T A    CMV-C CP
   546  A A G T A C G C C G T C C T C G T G T A    CMV-V34 CP
   828  A A G T A C G C C G T C C T G G T T T A    CMV-WL CP
   546  A A G T A C G C C G T C C T C G T G T A    CMV-V27 CP
   546  A A G T A C G C C G T C C T C G T G T A    CMV-V33 CP T T C A A A A G A C G A T G C G C T C G    Majority
                      950                 960
   566  T T C A A A A G A C G A T G C G C T C G    CMV-A35 CP
   938  T T C A A A A G A C G A T G C G C T C G    CMV-C CP
   566  T T C A A A A G A C G A T G C A C T C G    CMV-V34 CP
   848  C T C G A A A G A C G A T A A A C T A G    CMV-WL CP
   566  T T C A A A A G A C G A T G C G C T C G    CMV-V27 CP
   566  T T C A A A A G A C G A T G C A C T C G    CMV-V33 CP
```

FIG. 10I

```
    A G A C G G A C G A G C T A G T A C T T    Majority
                    970                 980
586  A G A C G G A C G A G C T A G T A C T T   CMV-A35 CP
958  A G A C G G A C G A G C T A G T A C T T   CMV-C CP
586  A G A C G G A C G A G C T A G T A C T T   CMV-V34 CP
868  A G A[A]G G A C G A G[A]T[T]G[C]A C T T   CMV-WL CP
586  A G A C G G A C G A G C T A G T A C T T   CMV-V27 CP
586  A G A C G G A C G A G C T A G T A C T T   CMV-V33 CP C A T G T T G A C A T C G A G C A C C A    Majority
                    990                1000
606  C A T G T T G A C A T C G A G C A C C A   CMV-A35 CP
978  C A T G T T G A C A T C G A G C A C C A   CMV-C CP
906  C A T G T T G A C A T C G A G C A C C A   CMV-V34 CP
888  C A T G T[C]G A C[G]T C G A G C A[T]C A   CMV-WL CP
606  C A T G T T G A C A T C G A G C A C C A   CMV-V27 CP
606  C A T G T T G A C[G]T C G A G C A C C A   CMV-V33 CP A C G C A T T C C C A C G T C T G G G G    Majority
                   1010                1020
626  A C G C A T T C C C A C G T C T G G[A]G   CMV-A35 CP
998  A C G C A T T C C C A C[A]T C T G G A G   CMV-C CP
626  A C G C A T T C C C A C G T C T G G G G   CMV-V34 CP
908  A C G[A]A T T C C[T]A[T]C T C[A C]G G[A]  CMV-WL CP
626  A C G[T]A T T C C C A C G T C T G G G A   CMV-V27 CP
626  A C G C A T T C C C A C G T C T G G G G   CMV-V33 CP T G C T C C C A G T C T G A T T C X T G    Majority
                   1030                1040
646  T G C T C C C A G T C T G A T T C . [T G] CMV-A35 CP
1018 T G C T C C C A G T C T G A T T C . [C]G  CMV-C CP
646  T G C T C C C A G T[T]T G A T T C . [C]G  CMV-V34 CP
928  T G C[T]C C C[G A C T]T A G T[C]C G[T G]  CMV-WL CP
646  T G C T C C C A G T C T G A T T C . [C]G  CMV-V27 CP
646  T G C T C C C A G T[A][A]A T T C .[T G]   CMV-V33 CP
```

FIG. 10J

```
      T G X T T C C C X X X X X X X X A G A A    Majority
                      1050              1060
 665  T G . T T C C C . . . . . . . . . A G A A  CMV-A35 CP
1037  T G . T T C C C . . . . . . . . . A G A A  CMV-C CP
 665  T G . T T C C . . . . . . . . . . A G A A  CMV-V34 CP
 948  T G T T T A C C G G C G T C C G A G A A    CMV-WL CP
 665  T G . T T C C C . . . . . . . . . A G A A  CMV-V27 CP
 665  T G C T T T C C . . . . . . . . . A G A A  CMV-V33 CP C C C T C C X C T C C G A T T T C T G T    Majority
                      1070              1080
 676  C C C T C C . C T C C G A T C T C T G T    CMV-A35 CP
1048  C C C T C C . C T C C G A T C T C T G T    CMV-C CP
 675  C C C T C C . C T C C G A T T T C T G T    CMV-V34 CP
 968  C G T A A A C T A C A C T C T C A A T      CMV-WL CP
 676  C C C T C C . C T C C G A T T T C T G T    CMV-V27 CP
 677  C C C T C C . C T C C G A T T T C T G T    CMV-V33 CP G G C G G G A G C T G A G T T G G C A G    Majority
                      1090              1100
 695  G G C G G G A G C T G A G T T G G C A G    CMV-A35 CP
1067  G G C G G G A G C T G A G T T G G C A G    CMV-C CP
 694  G G C G G G A G C T G A G T T G G C A G    CMV-V34 CP
 988  C G C G A G T G C T G A C T T G G T A G    CMV-WL CP
 695  G G C G G G A G C T G A G T T G G C A G    CMV-V27 CP
 696  G G C G G G A G C T G A G T T G G C A G    CMV-V33 CP T T C T G C T A T A A A C T G T C T G A    Majority
                      1110              1120
 715  T T C T G C T G T A A A C T G T C T G A    CMV-A35 CP
1087  T T C T A C T A C A A A C T G T C T G G    CMV-C CP
 714  T T C T G C T A T A A A C T G T C T G A    CMV-V34 CP
1008  T A T G C T T C A A A C T G C C T G A      CMV-WL CP
 715  T T C T G C T A T A A A C T G T C T G A    CMV-V27 CP
 716  T T C T G C T G T A A A C T G T C T G A    CMV-V33 CP
```

FIG. 10K

```
          A G T C A C T A A A C G T T T T A X X X    Majority
                             1130             1140
      735 │A G T C A C T A A A C G T T T T A│. . .   CMV-A35 CP
     1107 │A G T C A C T A A A C G T T T T A│. . .   CMV-C CP
      734 │A G T C A C T A A A C G T T T T A│. . .   CMV-V34 CP
     1028 │A G T C[C]C T A A A C G T[G]T T[G]T T G   CMV-WL CP
      735 │A G T C A C T A A A C G T T T[C]A│. . .   CMV-V27 CP
      736 │A G T C A C T A A A C G T T T T A│. . .   CMV-V33 CP X X C G G T G A A C G G G T T G T C C A Majority
                             1150             1160
      752 . .│C G G T G A A C G G G T T G T C C A│  CMV-A35 CP
     1124 . .│C G G T G A A C G G G T T G T C C A│  CMV-C CP
      751 . .│C G G T G A A C G G G T T G T C C A│  CMV-V34 CP
     1048 G G│C G G[G]G A A C G G G T[.]G T C C A│  CMV-WL CP
      752 . .│C G G T G A A C G G G T T G T C C A│  CMV-V27 CP
      736 . .│C G G T G A A C G G G T T G T C C A│  CMV-V33 CP T X X X X X X X X X X X X X X X X X X X    Majority
                             1170             1180
      770 │T│. . . . . . . . G G . . . . . . . .     CMV-A35 CP
     1142 │T│C C A G C T T A C G G C T A A A A T G   CMV-C CP
      769 │T│. . . . . . . . . . . . . . . . . .     CMV-V34 CP
     1067 │T│C C A G C T T A C G G C T A A A A T G   CMV-WL CP
      770 │T│. . . . . . . . . . . . . . . . . .     CMV-V27 CP
      771 │T│. . . . . . . . . . . . . . . . . .     CMV-V33 CP X X X X X X X X X X X X X X X X X X X X    Majority
                             1190             1200
      772  . . . . . . . . . . . . . . . . . . . .   CMV-A35 CP
     1162  G T C A . G T C G T G G A G A A A T C C   CMV-C CP
      770  . . . . . . . . . . . . . . . . . . . .   CMV-V34 CP
     1087  G T C G T G T C T T T C A . . . . . . C   CMV-WL CP
      771  . . . . . . . . . . . . . . . . . . . .   CMV-V27 CP
      772  . . . . . . . . . . . . . . . . . . . .   CMV-V33 CP
```

PLANTS RESISTANT TO CUCUMBER MOSAIC VIRUS STRAIN V34

This application is divisional of U.S. Ser. No. 09/616,567, filed Jul. 14, 2000, which is now U.S. Pat. No. 6,342,655, which is a divisional o U.S. Ser. No. 08/875,233, filed Sep. 29, 1997, which is a now U.S. Pat. No. 6,127,601, which is a 371 of PCT/US95/07234 filed Jun. 7, 1995 which is a continuation of U.S. Ser. No. 08/367,789, filed Dec. 30, 1994, now abandoned.

BACKGROUND OF THE INVENTION

1. Field of the Invention

This invention relates to coat protein (CP) genes derived from WT strains of cucumber mosaic virus (CMV). More specifically, the invention relates to the genetic engineering of plants and to a method for conferring viral resistance to a plant using an expression cassette encoding CP genes of WT strains of CMV.

2. Description of the Prior Art

Many agriculturally important crops are susceptible to infection by plant viruses, particularly CMV, which can seriously damage a crop, reduce its economic value to the grower, and increase its cost to the consumer. Attempts to control or prevent infection of a crop by a plant virus such as CMV have been made, yet viral pathogens continue to be a significant problem in agriculture.

Scientists have recently developed means to produce virus resistant plants using genetic engineering techniques. Such an approach is advantageous in that the genetic material which provides the protection is incorporated into the genome of the plant itself and can be passed on to its progeny. A host plant is resistant if it possesses the ability to suppress or retard the multiplication of a virus, or the development of pathogenic symptoms. "Resistant" is the opposite of "susceptible," and may be divided into: (1) high, (2) moderate, or (3) low resistance, depending upon its effectiveness. Essentially, a resistant plant shows reduced or no symptom expression, and virus multiplication within it is reduced or negligible. Several different types of host resistance to viruses are recognized. The host may be resistant to: (1) establishment of infection, (2) virus multiplication, or (3) viral movement.

CMV is a single-stranded (+) ribonucleic acid (RNA) plant virus that has a functionally divided genome. The virus genome contains four RNA species designated RNAs 1–4. RNs 3 and 4 encode the coat protein (CP) which is a protein that surrounds the viral RNA and protects the viral RNA from being degraded. Only RNAs 1–3 are required for infectivity because the CP, which is encoded by RNA 4, is also encoded by RNA 3.

Several strains of CMV have been classified using serology, host range, peptide mapping, nucleic acid hybridization, and sequencing analyses. These CMV strains can be divided into two groups, which are designated "WT" (also known as subgroup I) and "S" (also known as subgroup II). The S group consists of at least three members. The WT group is known to contain at least 17 members.

Expression of the CP genes from tobacco mosaic virus, alfalfa mosaic virus, CMV, and potato virus X, among others, in transgenic plants has resulted in plants which are resistant to infection by the respective virus. Heterologous protection can also occur. For example, the expression of CP genes from watermelon mosaic virus-2 (WMV-2) or zucchini yellow mosaic virus (ZYMV) in transgenic tobacco plants has been shown to confer protection against six other potyviruses: bean yellow mosaic virus, potato virus Y, pea mosaic virus, clover yellow vein virus, pepper mottle virus, and tobacco etch virus. However, expression of a preselected CP gene does not reliably confer heterologous protection to a plant. For example, transgenic squash plants containing the CMV-C CP gene, a WT virus, which have been shown to be resistant to the CMV-C strain are not protected to the same degree against several other, highly virulent WT strains of CMV.

Thus, a need exists for plants resistant to WT strains of CMV.

SUMMARY OF THE INVENTION

This invention provides: an isolated and purified deoxyribonucleic acid (DNA) molecule that encodes the CP for the V27 strain of CMV (CMV-V27), and a chimeric expression cassette comprising this DNA molecule; an isolated and purified DNA molecule that encodes the CP for the V33 strain of CMV (CMV-V33), and a chimeric expression cassette comprising this DNA molecule; and an isolated and purified DNA molecule that encodes the CP for the V34 strain of CMV (CMV-V34), and a chimeric expression cassette comprising this DNA molecule; and an isolated and purified DNA molecule that encodes the CP for the A35 strain of CMV (CMV-A35), and a chimeric expression cassette comprising the DNA molecule. Another embodiment of the invention is exemplified by the insertion of multiple virus gene expression cassettes into one purified DNA molecule, e.g., a plasmid. Each of these cassettes also includes a promoter which functions in plant cells to cause the production of an RNA molecule, and at least one polyadenylation signal comprising 3' nontranslated DNA which functions in plant cells to cause the termination of transcription and the addition of polyadenylated ribonucleotides to the 3' end of the transcribed messenger RNA (mRNA) sequences, wherein the promoter is operably linked to the DNA molecule, and the DNA molecule is operably linked to the polyadenylation signal. Preferably, these cassettes include the promoter of the 35S gene of cauliflower mosaic virus (CaMV-35S gene) and the polyadenylation signal of the CaMV-35S gene (CaMV-35S).

Also provided are bacterial cells, and transformed plant cells, containing the chimeric expression cassettes comprising the CP genes derived from the CMV-V27, CMV-V33, CMV-V34, or CMV-A35 strains, and preferably the 35S promoter and the polyadenylation signal of the CaMV-35S gene. Plants are also provided, wherein the plants comprise a plurality of transformed cells containing the chimeric CP gene expression cassettes derived from the CMV-V27, CMV-V33, CMV-V34, or CMV-A35 strains, and preferably the promoter and the polyadenylation signal of the CaMV gene. Transformed plants of this invention include tobacco, beets, corn, cucumber, peppers, potatoes, melons, soybean, squash, and tomatoes. Especially preferred are members of the *Cucurbitaceae* (e.g., squash and cucumber,) and *Solanaceae* (e.g., peppers and tomatoes) family.

Another aspect of the present invention is a method of preparing a CMV-resistant plant, such as a dicot, comprising: transforming plant cells with a chimeric expression cassette comprising a promoter functional in plant cells operably linked to a DNA molecule that encodes a CP of a WT strain of CMV, e.g., V27, V33, V34, or A35; regenerating the plant cells to provide a differentiated plant; and identifying a transformed plant that expresses the CMV CP at a level sufficient to render the plant resistant to infection by the specific strains of CMV disclosed herein.

As used herein, with respect to a DNA molecule or "gene," the phrase "isolated and purified" is defined to mean that the molecule is ether extracted from its context in the viral genome by chemical means and purified and/or modified to the extent that it can be introduced into the present vectors in the appropriate orientation, i.e., sense or antisense. As used herein, the term "chimeric" refers to the linkage of two or more DNA molecules which are derived from different sources, strains or species (e.g., from bacteria and plants), or the linkage of two or more DNA molecules, which are derived from the same species and which are linked in a way that does not occur in the native genome. As used herein, "expression" is defined to mean transcription or transcription followed by translation of a particular DNA molecule.

BRIEF DESCRIPTION OF THE DRAWINGS

FIG. 1A. The nucleotide sequence of the CP gene of CMV-V27 (hereinafter "CMV-V27 CP") from nucleotide position 1 to 360 (SEQ ID NO:1). The deduced amino acid sequence (SEQ ID NO:2) of the encoded open reading frame is shown below the nucleotide sequence.

FIG. 1B. The nucleotide sequence of the CP gene of CMV-V27 from nucleotide position 361 to 772 (SEQ ID NO:1). The deduced amino acid sequence (SEQ ID NO:2) of the encoded open reading frame is shown below the nucleotide sequence.

FIG. 2A. The nucleotide sequence of the CP gene of CMV-V33 (hereinafter "CMV-V33 CP") from nucleotide position 1 to 420 (SEQ ID NO:3). The deduced amino acid sequence (SEQ ID NO:4) of the encoded open reading frame is shown below the nucleotide sequence.

FIG. 2B. The nucleotide sequence of the CP gene of CMV-V33 from nucleotide position 421 to 773 (SEQ ID NO:3). The deduced amino acid sequence (SEQ ID NO:4) of the encoded open reading frame is shown below the nucleotide sequence.

Figure 3:
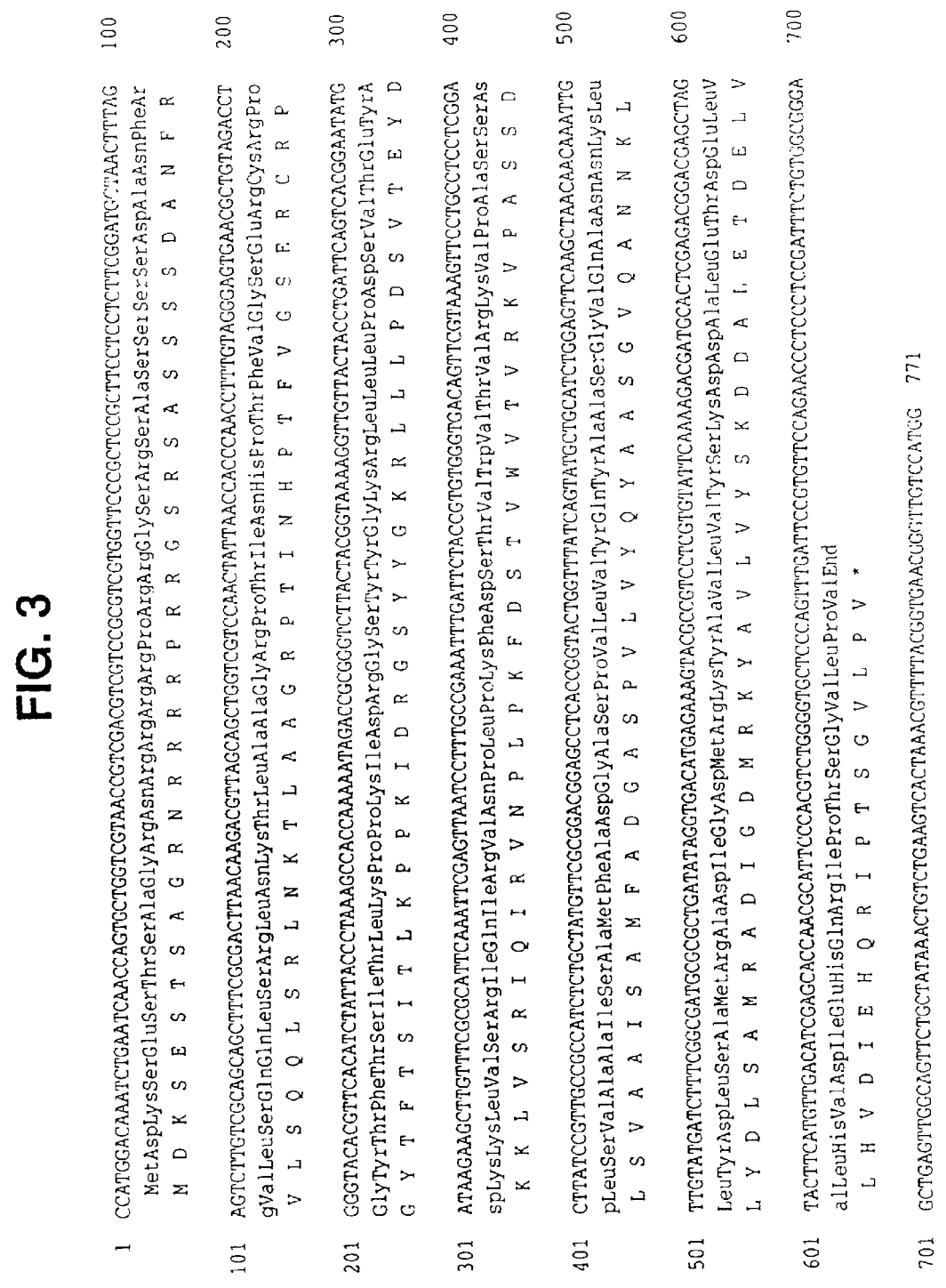

FIG. 3. The nucleotide sequence of the CP gene of CMV-V34 (hereinafter "CMV-34 CP") from nucleotide position 1 to 771 (SEQ ID NO:5). The deduced amino acid sequence (SEQ ID NO:6) of the encoded open reading frame is shown below the nucleotide sequence.

FIG. 4A. The alignment of the nucleotide sequences of the CP genes from five CMV strains from nucleotide position 1 to 600. CMV-C CP (SEQ ID NO: 9) and CMV-WL CP (SEQ ID NO: 11) are described in Quemada et al. (*J. Gen. Viral.* 70:1065 1989)). The nucleotide sequence of CMV-V27 CP is shown in SEQ ID NO: 1, CMV-V33 CP is SEQ ID NO: 3 and CMV-V34 CP is SEQ ID NO: 5. Alignments were obtained with the use of the UWGCG Pileup program. The dots represent either the lack of sequence information at the 5' end of the CP gene or gaps in homology in sequences relative to others in the alignment. The position of primer RMM351 is shown (SEQ ID NO: 7).

FIG. 4B. The alignment of the nucleotide sequences of the CP genes from five CMV strains (SEQ ID NOS: 1, 3, 5, 9 and 11) described in FIG. 4A from nucleotide position 601 to 840.

FIG. 4C. The alignment of the nucleotide sequences of the CP genes from five CMV strains (SEQ ID NOS: 1, 3, 5, 9 and 11) described in FIG. 4A from nucleotide position 841 to 1080.

FIG. 4D. The alignment of the nucleotide sequences of the CP genes from five CMV strains (SEQ ID NOS: 1, 3, 5, 9 and 11) from nucleotide position 1081 to 1170 alignment. The position of primer RMM352 is shown (SEQ ID NO: 8).

FIG. 5A. The alignment of the sequences of amino acid 1–150 deduced from the nucleotide sequences of CMV strains CMV-V27 CP (SEQ ID NO: 2), CMV-V33 CP (SEQ ID NO: 4), CMV-V34 CP (SEQ ID NO: 6), CMV-C CP (SEQ ID NO: 10) (shown in FIG. 4) and CMV strain Cmvq3 (Quemada et al., *J. Gen. Virol.* 70:1065 (1989)) (SEQ ID NO: 13) (hereinafter referred to as "CMV-Q3 CP"). The amino acid sequence of CMV-WL CP is shown in SEQ ID NO: 12. Alignments were performed by the UWGCG Pileup program. Differences among the WT virus strains are underlined and highlighted with asterisks. The dots represent gaps in homology in sequences relative to others in the alignment.

FIG. 5B. The alignment of the sequences of amino acid 151–219 deduced from the nucleotide sequences of CMV strains as described in FIG. 5A. (SEQ ID NOS: 2, 4, 6, 10, 12 and 13).

(FIG. 6A, continued.) Insertion of a CMV-V27 CP expression cassette BamHI fragment into the BglII site of pEPG204 and pEPG205 to produce pEPG239 and pEPG240, respectively.

(FIG. 7A, continued.) Insertion of a CMV-V33 CP expression cassette BamHI fragment into the BglII site of pEPG204 and pEPG205 to produce pEPG196 and pEPG197, respectively.

FIG. 8. The nucleotide sequence of the CP gene of CMV-A35 (SEQ ID NO: 14) (hereinafter "CMV-A35 CP"). The deduced amino acid sequence of the encoded open reading frame is shown below the nucleotide sequence (SEQ ID NOS: 15–19).

FIG. 9A. The alignment of the amino acid sequences deduced from the nucleotide sequences of the six CMV strains shown in FIG. 10A for amino acid 1–120. (The majority is shown in SEQ ID NO: 20, CMV-C CP AA SEQ is SEQ ID NO: 10, CMV-C-A35 CP is SEQ ID NO: 15, CMV-V27 CP AA SEQ is SEQ ID NO: 2, CMV-V33 CP AA SEQ is SEQ ID NO: 4, CMV-V34 CP AA SEQ is SEQ ID NO: 6, and CMV-WL CP AA SEQ is SEQ ID NO: 12). Differences among the coat proteins are enclosed in boxes. The dashes represent gaps in homology in sequences relative to others in the alignment.

FIG. 9B. The alignment of the amino acid sequences deduced from the nucleotide sequences of the six CMV strains shown in FIG. 10 for amino acid 121 to 220 (SEQ ID NOS: 2, 4, 6, 10, 12 and 15).

FIG. 10A. The alignment of the nucleotide sequences of the CP genes from 6 CMV strains from nucleotide position 321–400 of a consensus sequence The majority is shown in SEQ ID NO: 21, CMV C-A35 CP is SEQ ID NO: 14, CMV-C CP is SEQ ID NO: 9, New CMV-V34 CP is SEQ ID NO: 5, CMV-WL CP is SEQ ID NO. 11, CMV-V27 CP is SEQ ID NO: 1 and CMV-V33 CP is SEQ ID NO: 3.). The dots represent either the lack of sequence information at the 5' end of the CP gene or gaps in homology in sequences relative to others in the alignment.

FIG. 10B. The alignment of the nucleotide sequences of the CP genes of CMV strains described in FIG. 10A from nucleotide position 401 to 480 (SEQ ID NOS: 1, 3, 5, 9, 11, 14 and 21).

FIG. 10C. The alignment of the nucleotide sequences of the CP genes of CMV strains described in FIG. 10A from nucleotide position 481 to 560 (SEQ ID NOS: 1, 3, 5, 9, 11, 14 and 21).

FIG. 10D. The alignment of nucleotide sequences of the CP genes of CMV strains described in FIG. 10A from nucleotide position 561 to 640 (SEQ ID NOS: 1, 3, 5, 9, 11, 14 and 21).

FIG. 10E. The alignment of the nucleotide sequences of the CP genes of CMV strains described in FIG. 10A from nucleotide position 641 to 720 (SEQ ID NOS: 1, 3, 5, 9, 11, 14 and 21).

FIG. 10F. The alignment of the nucleotide sequences of the CP genes of CMV strains described in FIG. 10A from nucleotide position 721 to 800 (SEQ ID NOS: 1, 3, 5, 9, 11, 14 and 21).

FIG. 10G. The alignment of he nucleotide sequences of the CP genes of CMV strains described in FIG. 10A from nucleotide position 801 to 880 (SEQ ID NOS: 1, 3, 5, 9, 11, 14 and 21).

FIG. 10H. The alignment of the nucleotide sequences of the CP genes of CMV strains described in FIG. 10A from nucleotide position 881 to 960 (SEQ ID NOS: 1, 3, 5, 9, 11, 14 and 21).

FIG. 10I. The alignment of the nucleotide sequences of the CP genes of CMV strains described in FIG. 10A from nucleotide position 961 to 1040 (SEQ ID NOS: 1, 3, 5, 9, 11, 14 and 21).

FIG. 10J. The alignment of the nucleotide sequences of the CP genes of CMV strains described in FIG. 10A from nucleotide position 1041 to 1120 (SEQ ID NOS: 1, 3, 5, 9, 11, 14 and 21).

FIG. 10K. The alignment of the nucleotide sequences of the CP genes of CMV strains described in FIG. 10A from nucleotide position 1121 to 1200. The dots represent gaps in homology in sequences relative to others in the alignment (SEQ ID NOS: 1, 3, 5, 9, 11, 14 and 21).

DETAILED DESCRIPTION OF THE INVENTION

Figure 6A:
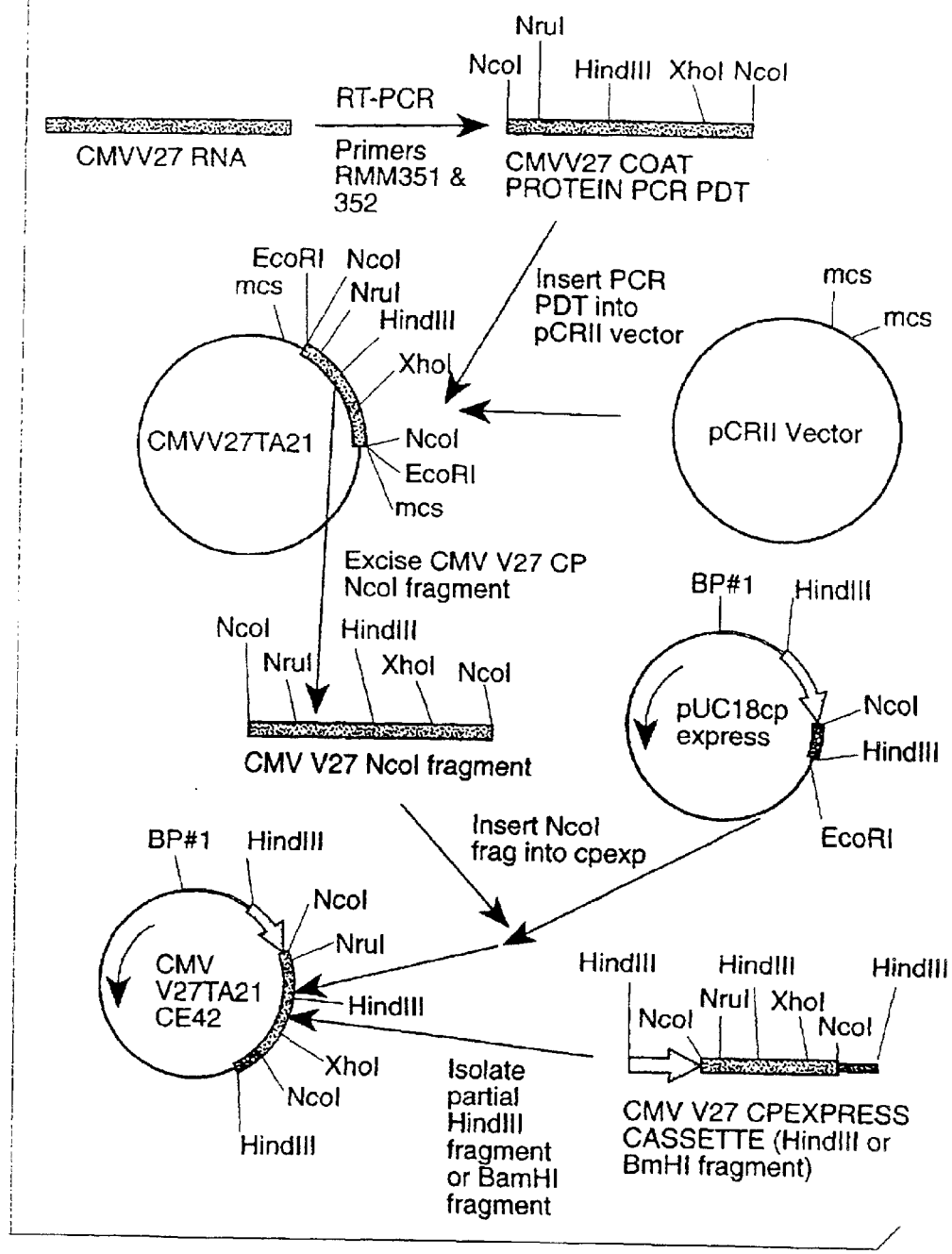
FIG. 6A. Assembly of CMV-V27 CP expression cassette. Polymerase chain reaction (PCR) products of CMV-V27 were installed into pCRII and subsequently inserted into pUC18cpexpress by routine methods. The bolded lines and arrows which are a part of the circle represent CaMV-35S sequences.

The genome of CMV contains four RNA species designated RNA 1, 2, 3 and 4; 3389 nucleotides (nt), 3035 nt, 2193 nt, and 1027 nt, respectively (Peden et al., Virol., 53:487 (1973); Gould et al., Eur. J. Biochem., 126:217 (1982); Rezaian et al., Eur. J. Biochem., 143:227 (1984); Rezaian et al., Eur. J. Biochem. 150:331 (1985)). Only RNA 1, 2 and 3 are required for infectivity (Peden et al., Virol., 53:487 (1973)) because the CP, which is encoded by RNA 4, is also encoded by RNA 3. Translation of CMV RNA yield a 95 kiloDalton (kD) polypeptide from RNA 1, a 94 kD polypeptide from RNA 2 (Gordon et al., Virol., 123:284 (1983)), and two polypeptides from RNA 3: its 5' end encodes a 35 kD polypeptide, and its 3' end encodes a 24.5 kD polypeptide (Gould et al., Eur. J. Biochem., 126:217 (1982)). The 24.5 kD polypeptide is identical to that encoded by RNA 4 and is the CP.

Several strains of CMV have been classified using serology, host range, peptide mapping, nucleic acid hybridization, and sequencing. These CMV strains include two groups, WT and S. CMV WT strains include CMV-C, CMV-V27, CMV-V33, CMV-V34, CMV-M, CMV-O, CMV-Y, and CMV-A35 while S strains include CMV-Q, CMV-WL, and CMV-LS (Zaitlin et al., Viral., 201:200 (1994)). Protection against a strain in one group does not necessarily provide protection against all strains in that group. For example, transgenic squash plants protected with CP genes from the CMV-C are not protected against the CMV strains V27, V33, V34, or A35. In addition, Zaitlin et al. (Virol., 201:200 (1994)) report that tobacco plants transgenic for a CMV-FNY replicase gene show protection against challenge from WT strains but show no protection against challenge from S strain challenges. Thus, the present invention is directed to providing plants with resistance to WT strains of CMV, e.g., V27, V33, V34, or A35.

To practice the present invention, a viral gene must be isolated from the viral genome and inserted into a vector. Thus, the present invention provides isolated and purified DNA molecules that encode the CP of the V27, V33, or V34 strains of CMV. As used herein, a DNA molecule that encodes a CP gene includes nucleotides of the coding strand, also referred to as the "sense" strand, as well as nucleotides of the noncoding strand, complementary strand, also referred to as the "antisense" strand, either alone or in their base-paired configuration. Thus, a DNA molecule that encodes the CP of the V27 strain of CMV, for example, includes the DNA molecule having the nucleotide sequence of FIG. 1, a DNA molecule complementary to the nucleotide sequence of FIG. 1, as well as a DNA molecule which also encodes a CMV CP and its complement which hybridizes with a CMV-V27-specific DNA probe in hybridization buffer with 6×SSC, 5× Denhardt's reagent, 0.5% SDS and 100 micrograms per milliliter ($\mu$g/ml) denatured, fragmented salmon sperm DNA and remains bound when washed at 68° in 0.1×SSC and 0.5% SDS (Sambrook et al., MOLECULAR CLONING: A LABORATORY MANUAL, 2nd ed. (1989)). Moreover, the DNA molecules of the present invention can include non-CMV CP nucleotides that do not interfere with expression of the CMV CP gene. Preferably, the isolated and purified DNA molecules of the present invention comprise a single coding region for the CP. Thus, preferably the DNA molecules of the present invention are those consisting essentially of DNA that encodes the CP.

These CMV genes are used to produce the CPs, which are believed to confer resistance to viruses. Another molecular strategy to provide virus resistance in transgenic plants is based on antisense RNA. As is well known, a cell manufactures protein by transcribing the DNA of the gene encoding that protein to produce RNA, which is then processed to mRNA (e.g., by the removal of introns) and finally translated by ribosomes into protein. This process may be inhibited in the cell by the presence of antisense RNA. The term antisense RNA means an RNA sequence which is complementary to a sequence of bases in the mRNA in question in the sense that each base (or the majority of bases) in the antisense sequence (read in the 3' to 5' sense) is capable of pairing with the corresponding base (G with C, A with U) in the mRNA sequence read in the 5' to 3' sense. It is believed that this inhibition takes place by formation of a complex between the two complementary strands of RNA, thus preventing the formation of protein. How this works is uncertain: the complex may interfere with further transcription, processing, transport or translation, or degrade the mRNA, or have more than one of these effects. This antisense RNA may be produced in the cell by transformation of the cell with an appropriate DNA construct arranged to transcribe the non-template strand (as opposed to the template strand) of the relevant gene (or of a DNA sequence showing substantial homology therewith).

The use of antisense RNA to downregulate the expression of specific plant genes is well known. Reduction of gene expression has led to a change in the phenotype of the plant: either at the level of gross visible phenotypic difference, e.g., lack of anthocyanin production in flower petals of petunia leading to colorless instead of colored petals (van der Krol et al., Nature, 333:866–869 (1988)); or at a more subtle biochemical level, e.g., change in the amount of polygalacturonase and reduction in depolymerization of pectin during tomato fruit ripening (Smith et al., Nature, 334:724–726 (1988)).

Another more recently described method of inhibiting gene expression in transgenic plants is the use of sense RNA transcribed from an exogenous template to downregulate the expression of specific plant genes (Jorgensen, Keystone Symposium "Improved Crop and Plant Products through Biotechnology", Abstract X1-022 (1994)). Thus, both antisense and sense RNA have been proven to be useful in achieving downregulation of gene expression in plants, which are encompassed by the present invention.

The CMV CP gene does not contain the signals necessary for its expression once transferred and integrated into a plant genome. Accordingly, a vector must be constructed to provide the regulatory sequences such that they will be functional upon inserting a desired gene. When the expression vector/insert construct is assembled, it is used to transform plant cells which are then used to regenerate plants. These transgenic plants carry the viral gene in the expression vector/insert construct. The gene is expressed in the plant and increased resistance to viral infection is conferred thereby.

Several different methods exist to isolate a viral gene. To do so, one having ordinary skill in the art can use information about the genomic organization of cucumoviruses to locate and isolate the CP gene. The CP gene is located near the 3' end of RNA 3. Using methods well known in the art, a quantity of virus is grown and harvested. The viral RNA is then separated by gel electrophoresis. A cDNA library is created using the viral RNA, by methods known to the art. The viral RNA is incubated with primers that hybridize to the viral RNA and reverse transcriptase, and a complementary DNA molecule is produced. A DNA complement of the complementary DNA molecule is produced and that sequence represents a DNA copy (cDNA) of the original viral RNA molecule. The DNA complement can be produced in a manner that results in a single double stranded cDNA or PCR can be used to amplify the DNA encoding the cDNA with the use of oligomer primers specific for viral sequences. These primers can include novel restriction sites used in subsequent cloning steps. Thus, a double stranded DNA molecule is generated which contains the sequence information of the viral RNA. These DNA molecules can be cloned in *E. coli* plasmid vectors after the additions of restriction enzyme linker molecules by DNA ligase. The various fragments are inserted into cloning vectors, such as well-characterized plasmids, which are then used to transform *E. coli* and create a cDNA library. CMV CP genes from previously isolated strains can be used as hybridization probes to screen the cDNA library to determine if any of the transformed bacteria contain DNA fragments with sequences coding for a CMV CP. Alternatively, plasmids which harbor CMV CP sequences can be determined by restriction enzyme digestion of plasmids in bacterial transformants. The cDNA inserts in any bacterial colonies which contain this region can be sequenced. The CP gene is present in its entirety in colonies which have sequences that extend 5' to the sequence which encodes the ATG start codon and sequences that extend 3' of the stop codon.

Alternatively, cDNA fragments can be inserted in the sense orientation into expression vectors. Antibodies against the CP can be used to screen the cDNA expression library and the gene can be isolated from colonies which express the protein.

In the present invention, the DNA molecules encoding the CP genes of the CMV strains V27, V33, V34, and A35 have been determined and the genes have been inserted into expression cassettes. These expression cassettes can be individually placed into a vector that can be transmitted into plants, preferably a binary vector. Alternatively, two or more of the CMV CP genes can each be present in an expression cassette which can be placed into the same binary vector, or any of the CMV CP expression cassettes of the present invention can be placed into a binary vector with one or more viral gene expression cassettes. The expression vectors contain the necessary genetic regulatory sequences for expression of an inserted gene. The CP gene is inserted such that those regulatory sequences are functional and the genes can be expressed when incorporated into a plant genome. For example, vectors of the present invention can contain combinations of expression cassettes that include DNA from a heterologous CMV CP gene (i.e., one from another CMV isolate), papaya ringspot virus (PRV) CP gene, a ZYMV CP gene, and a WMV-2 CP gene.

Moreover, when combinations of viral gene expression cassettes are placed in the same binary plasmid, and that multigene cassette containing plasmid transformed into a plant, the viral genes all preferably exhibit substantially the same degrees of efficacy when present in transgenic plants. For example, if one examines numerous transgenic lines containing two different intact viral gene cassettes, the transgenic line will be immune to infection by both viruses. Similarly, if a line exhibits a delay in symptom development to one virus, it will also exhibit a delay in symptom development to the second virus. Finally, if a line is susceptible to one of the viruses it will be susceptible to the other. This phenomenon is unexpected. If there were not a correlation between the efficacy of each gene in these multiple gene constructs this approach as a tool in plant breeding would probably be prohibitively difficult to use. Even with single gene constructs, one must test numerous transgenic plant lines to find one that displays the appropriate level of efficacy. The probability of finding a line with useful levels of expression can range from 10–50% (depending on the species involved). For further information refer to Applicants' International Patent Application No.

PCT/US95/06261 entitled "Transgenic Plants Expressing DNA Constructs Containing a Plurality of Genes to Impart Virus Resistance" filed on Jun. 7, 1995, incorporated by reference herein.

In order to express the viral gene, the necessary genetic regulatory sequences must be provided. In the present invention, the CP genes are inserted into vectors which contain cloning sites for insertion 3' of the initiation codon and 5' of the poly(A) signal. The promoter is 5' of the initiation codon such that when genes are inserted at the cloning site, a functional unit is formed in which the inserted genes are expressed under the control of the various genetic regulatory sequences.

The segment of DNA referred to as the promoter is responsible for the regulation of the transcription of DNA into mRNA. A number of promoters which function in plant cells are known in the art and can be employed in the practice of the present invention. These promoters can be obtained from a variety of sources such as plant or plant viruses, and can include, but are not limited to, promoters isolated from the caulimovirus group such as the CaMV-35S promoter (CaMV-35S), the enhanced CaMV-35S promoter (enh-CaMV-35S), the figwort mosaic virus full-length transcript promoter FMV-34S), and the promoter isolated from the chlorophyll a/b binding protein. Other useful promoters include promoters which are capable of expressing the cucumovirus proteins in an inducible manner or in a tissue-specific manner in certain cell types in which the infection is known to occur. For example, the inducible promoters from phenylalanine ammonia lyase, chalcone synthase, hydroxyproline rich glycoprotein, extensin, pathogenesis-related proteins (e.g. PR-1a), and wound-inducible protease inhibitor from potato may be useful.

Preferred promoters for use in the present CP-containing cassettes include the constitutive promoters from CaMV, the tumor-inducing (Ti) genes nopaline synthase (NOS) (Bevan et al., Nucleic Acids Res., 11:369 (1983)) and octopine synthase (Depicker et al., J. Mol. Appl. Genet., 1:561 (1982)), and the bean storage protein gene phaseolin. The poly(A) addition signals from these genes are also suitable for use in the present cassettes. The particular promoter selected is preferably capable of causing sufficient expression of the DNA coding sequences to which it is operably linked, to result in the production of RNA or proteins effective to provide viral resistance, but not so much as to be detrimental to the cell in which they are expressed. The promoters selected should be capable of functioning in tissues including, but not limited to, epidermal, vascular, and mesophyll tissues. The actual choice of the promoter is not critical, as long as it has sufficient transcriptional activity of their respective RNAs to accomplish the expression of the preselected proteins and their subsequent conferral of viral resistance to the plants.

The nontranslated leader sequence can be derived from any suitable source and can be specifically modified to increase the translation of the mRNA. The 5' nontranslated region can be obtained from the promoter selected to express the gene, an unrelated promoter, the native leader sequence of the gene or coding region to be expressed, viral RNAs, suitable eucaryotic genes, or a synthetic gene sequence. The present invention is not limited to the constructs presented in the following examples.

The termination region or 3' nontranslated region which is employed is one which will cause the termination of transcription and the addition of polyadenylated ribonucleotides to the 3' end of the transcribed mRNA sequence. The termination region can be native with the promoter region, native with the gene, or can be derived from another source, and preferably include a terminator and a sequence coding for polyadenylation. Suitable 3' nontranslated regions of the chimeric plant gene include but are not limited to: (1) the 3' transcribed, nontranslated regions containing the polyadenylation signal of Agrobacterium Ti plasmid genes, such as the NOS gene; and (2) plant genes like the soybean 7S storage protein genes.

Preferably, the expression cassettes of the present invention are engineered to contain a constitutive promoter 5' to its translation initiation codon (ATG) and a poly(A) addition signal (AATAAA) 3' to its translation termination codon. Several promoters which function in plants are available, however, the preferred promoter is the 35S constitutive promoters from CaMV. The poly (A) signal can be obtained from the CaMV-35S gene or from any number of well characterized plant genes, i.e., NOS, octopine synthase, and the bean storage protein gene phaseolin. The constructions are similar to that used for the expression of the CMV-C CP in PCT Patent Application PCT/US88/04321, published on Jun. 29, 1989 as WO 89/05858, claiming the benefit of U.S. Ser. No. 135,591, filed Dec. 21, 1987, entitled "Cucumber Mosaic Virus Coat Protein Gene", and the CMV WL CP in PCT Patent Application PCT/US89/03288, published on Mar. 8, 1990 as WO 90/02185, claiming the benefit of U.S. Ser. No. 234,404, filed Aug. 19, 1988, entitled "Cucumber Mosaic Virus Coat Protein Gene."

Selectable marker genes can be incorporated into the present expression cassettes and used to select for those cells or plants which have become transformed. The marker gene employed may express resistance to an antibiotic, such as kanamycin, gentamycin, G418, hygromycin, streptomycin, spectinomycin, tetracycline, chloramphenicol, and the like. Other markers could be employed in addition to or in the alternative, such as, for example, a gene coding for herbicide tolerance such as tolerance to glyphosate, sulfonylurea, phosphinothricin, or bromoxynil. Additional means of selection could include resistance to methotrexate, heavy metals, complementation providing prototrophy to an auxotrophic host, and the like.

The particular marker employed will be one which will allow for the selection of transformed cells as opposed to those cells which are not transformed. Depending on the number of different host species one or more markers can be employed, where different conditions of selection would be useful to select the different host, and would be known to those of skill in the art. A screenable marker such as the β-glucuronidase gene can be used in place of, or with, a selectable marker. Cells transformed with this gene can be identified by the production of a blue product on treatment with 5-bromo-4-chloro-3-indoyl-β-D-glucuronide.

In developing the present expression construct, i.e., expression cassette, the various components of the expression construct such as the DNA molecules, linkers, or fragments thereof will normally be inserted into a convenient cloning vector, such as a plasmid or phage, which is capable of replication in a bacterial host, such as E. coli. Numerous cloning vectors exist that have been described in the literature. After each cloning, the cloning vector can be isolated and subjected to further manipulation, such as restriction, insertion of new fragments, ligation, deletion, resection, insertion, in vitro mutagenesis, addition of polylinker fragments, and the like, in order to provide a vector which will meet a particular need.

For Agrobacterium-mediated transformation, the expression cassette will be included in a vector, and flanked by fragments of the *Agrobacterium* Ti or root-inducing (Ri) plasmid, representing the right and, optionally the left, borders of the Ti or Ri plasmid transferred DNA (T-DNA). This facilitates integration of the present chimeric DNA sequences into the genome of the host plant cell. This vector will also contain sequences that facilitate replication of the plasmid in *Agrobacterium* cells, as well as in *E. coli* cells.

All DNA manipulations are typically carried out in *E. coli* cells, and the final plasmid bearing the cucumovirus expression cassette is moved into *Agrobacterium* cells by direct DNA transformation, conjugation, and the like. These *Agrobacterium* cells will contain a second plasmid, also derived from Ti or Ri plasmids. This second plasmid will carry all the vir genes required for transfer of the foreign DNA into plant cells. Suitable plant transformation cloning vectors include those derived from a Ti plasmid of *Agrobacterium tumefaciens*, as generally disclosed in Glassman et al. (U.S. Pat. No. 5,258,300), or *Agrobacterium rhizogenes*.

A variety of techniques are available for the introduction of the genetic material into or transformation of the plant cell host. However, the particular manner of introduction of the plant vector into the host is not critical to the practice of the present invention, and any method which provides for efficient transformation can be employed. In addition to transformation using plant transformation vectors derived from the Ti or Ri plasmids of *Agrobacterium*, alternative methods could be used to insert the DNA constructs of the present invention into plant cells. Such methods may include, for example, the use of liposomes, electroporation (Fromm et al., Proc. Natl. Acad. Sci. USA, 82:824 (1984)), chemicals that increase the free uptake of DNA (Paszkowski et al., EMBO J., 3:2717 (1984)), DNA delivery via microprojectile bombardment (Klein et al., Nature, 327:70 (1987)), microinjection (Crossway et al., Mol. Gen. Genet., 202:179 (1985)), and transformation using viruses or pollen.

The choice of plant tissue source or cultured plant cells for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is regenerable, in that it will retain the ability to regenerate whole, fertile plants following transformation.

The transformation is carried out under conditions directed to the plant tissue of choice. The plant cells or tissue are exposed to the DNA carrying the present viral gene expression cassette(s) for an effective period of time. This can range from a less-than-one-second pulse of electricity for electroporation, to a two-to-three day co-cultivation in the presence of plasmid-bearing *Agrobacterium* cells. Buffers and media used will also vary with the plant tissue source and transformation protocol. Many transformation protocols employ a feeder layer of suspended culture cells (tobacco or Black Mexican Sweet Corn, for example) on the surface of solid media plates, separated by a sterile filter paper disk from the plant cells or tissues being transformed.

Following treatment with DNA, the plant cells or tissue may be cultivated for varying lengths of time prior to selection, or may be immediately exposed to a selective agent such as those described hereinabove. Protocols involving exposure to *Agrobacterium* will also include an agent inhibitory to the growth of the *Agrobacteriun* cells. Commonly used compounds are antibiotics such as cefotaxime and carbenicillin The media used in the selection may be formulated to maintain transformed callus or suspension culture cells in an undifferentiated state, or to allow production of shoots from callus, leaf or stem segments, tuber disks, and the like.

Cells or callus observed to be growing in the presence of normally inhibitory concentrations of the selective agents are presumed to be transformed and may be subcultured several additional times on the same medium to remove nonresistant sections. The cells or calli can then be assayed for the presence of the viral gene cassette, or can be subjected to known plant regeneration protocols. In protocols involving the direct production of shoots, those shoots appearing on the selective media are presumed to be transformed and can be excised and rooted, either on selective medium suitable for the production of roots, or by simply dipping the excised shoot in an Ri compound and directly planting it in vermiculite.

In order to produce transgenic plants exhibiting viral resistance, the viral genes must be taken up into the plant cell and stably integrated within the plant genome. Plant cells and tissues selected for their resistance to an inhibitory agent are presumed to have acquired the selectable marker gene encoding this resistance during the transformation treatment. Since the marker gene is commonly linked to the viral genes, it can be assumed that the viral genes have similarly been acquired. Southern blot hybridization analysis using a probe specific to the viral genes can then be used to confirm that the foreign genes have been taken up and integrated into the genome of the plant cell. This technique may also give some indication of the number of copies of the gene that have been incorporated. Successful transcription of the foreign gene into mRNA can likewise be assayed using Northern blot hybridization analysis of total cellular RNA and/or cellular RNA that has been enriched in a polyadenylated region. mRNA molecules encompassed within the scope of the invention are those which contain viral specific sequences derived from the viral genes present in the transformed vector which are of the same polarity as that of the viral genomic RNA such that they are capable of base pairing with viral specific RNA of the opposite polarity to that of viral genomic RNA under conditions described in Chapter 7 of Sambrook et al. (1989). Moreover, mRNA molecules encompassed within the scope of the invention are those which contain viral specific sequences derived from the viral genes present in the transformed vector which are of the opposite polarity as that of the viral genomic RNA such that they are capable of base pairing with viral genomic RNA under conditions described in Chapter 7 in Sambrook et al. (1989).

The presence of a viral gene can also be detected by immunological assays, such as the double-antibody sandwich assays described by Namba et al., Gene, 107:181 (1991) as modified by Clark et al., J. Gen. Virol., 34:475 (1979). See also, Namba et al., Phytopathology, 82:940 (1992). Cucumovirus resistance can also be assayed via infectivity studies as generally disclosed by Namba et al., ibid., wherein plants are scored as symptomatic when any inoculated leaf shows vein clearing, mosaic or necrotic symptoms.

Seed from plants regenerated from tissue culture is grown in the field and self-pollinated to generate true breeding plants. The progeny from these plants become true breeding lines which are evaluated for viral resistance in the field under a range of environmental conditions. The commercial value of viral-resistant plants is greatest if many different hybrid combinations with resistance are available for sale. The farmer typically grows more than one kind of hybrid based on such differences as maturity, color or other agronomic traits. Additionally, hybrids adapted to one part of a country are not adapted to another part because of differences in such traits as maturity, disease and insect tolerance. Because of this, it is necessary to breed viral resistance into a large number of parental lines so that many hybrid combinations can be produced.

The invention will be further described by reference to the following detailed examples. Enzymes were obtained from commercial sources and were used according to the vendor's recommendations or other variations known in the art. Other reagents, buffers, etc., were obtained from commercial sources, such as Sigma Chemical Co., St. Louis, Mo., unless otherwise specified.

Most of the recombinant DNA methods employed in practicing the present invention are standard procedures, well known to those skilled in the art, and described in detail in, for example, in European Patent Application Publication Number 223,452, published Nov. 29, 1986, which is incorporated herein by reference. General references containing such standard techniques include the following: R. Wu, ed., METHODS IN ENZYMOLOGY, Vol. 68 (1979); J. H. Miller, EXPERIMENTS IN MOLECULAR GENETICS (1972); J. Sambrook et al., MOLECULAR CLONING: A LABORATORY MANUAL, 2nd ed. (1989); and D. M. Glover, ed , DNA CLONING VOL. II (1982).

Figure 6B:
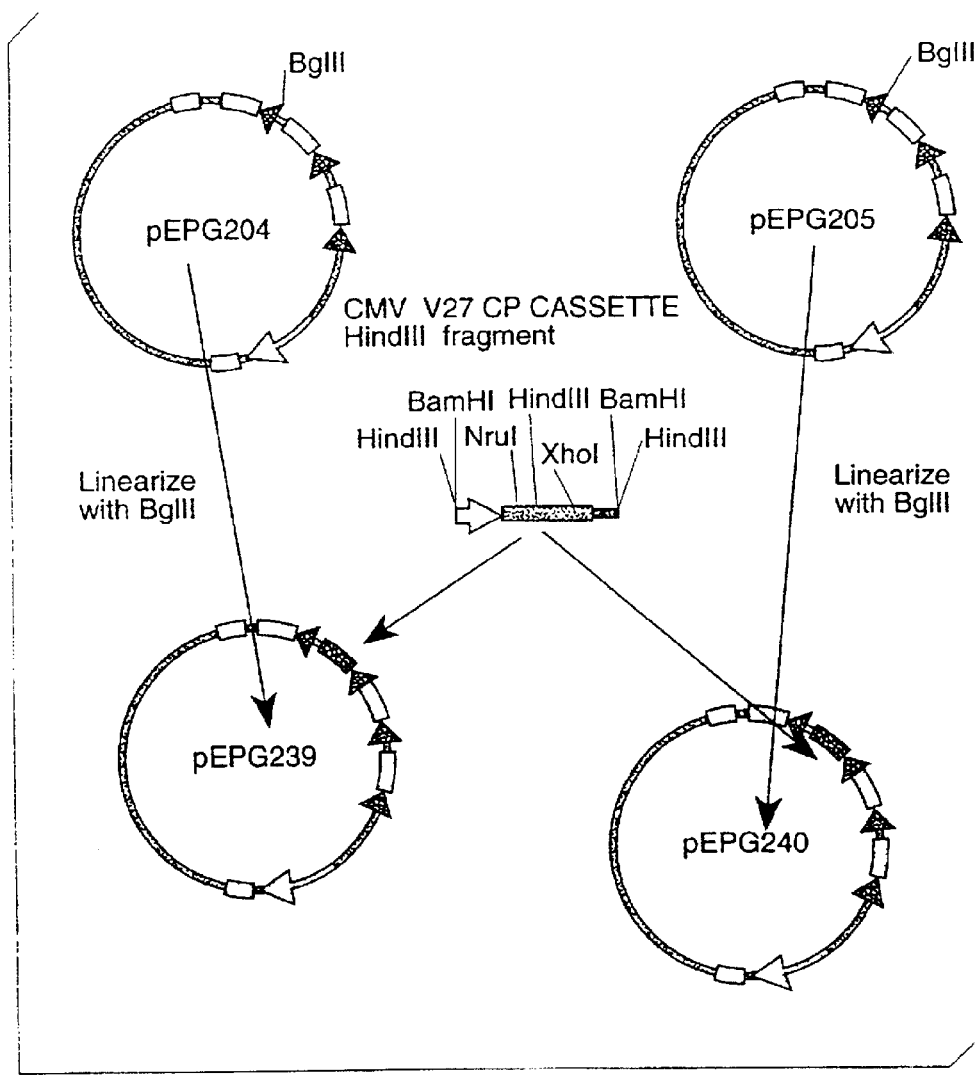
FIG. 6B.
Figure 6C:
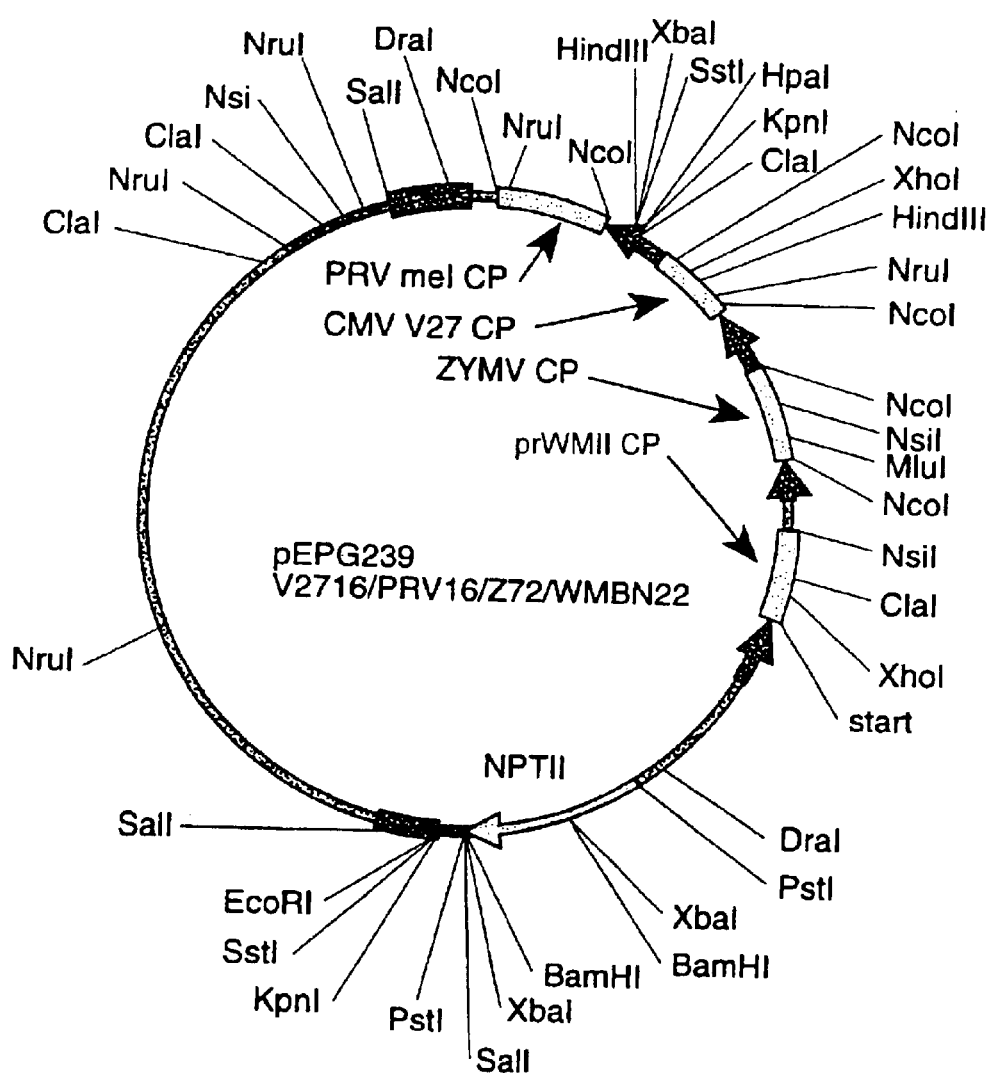
FIG. 6C. Restriction map of pEPG239. This binary plasmid includes the CP expression cassettes for PRV (melon, long), CMV-V27 CP, ZYMV CP, and WMVII CP. For further information on PRV CP genes, refer to Applicants' International Patent Application No. PCT/US95/07272 entitled "Papaya Ringspot Virus Coat Protein Gene" filed on Jun. 7, 1995, incorporated by reference herein. For further information on ZYMV and WMV-2 CP genes, refer to Applicants' International Patent Application No. PCT/US89/03094 filed on Jul. 20, 1989 entitled "Potyvirus Coat Protein Genes and Plants Transformed Therewith", incorporated by reference herein.
Figure 6D:
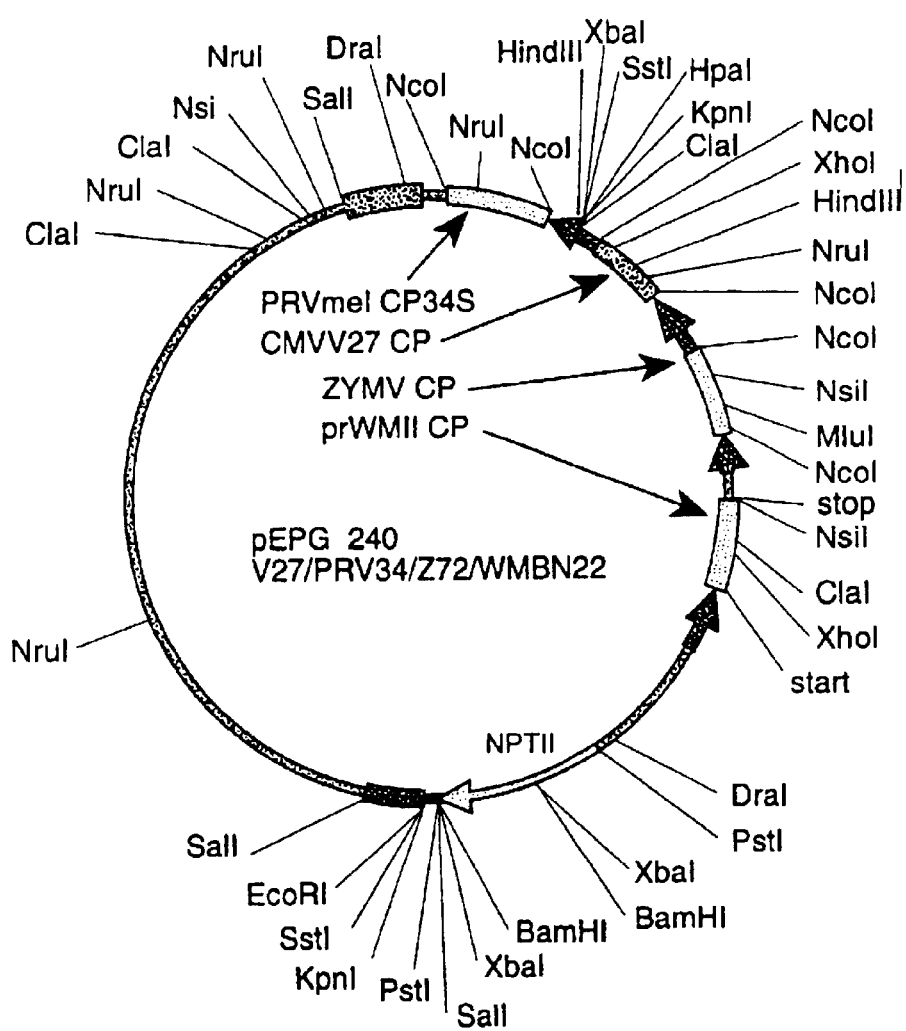
FIG. 6D. Restriction map of pEPG240. This binary plasmid includes the CP expression cassettes for PRV (melon, short), CMV-V27 CP, ZYMV CP, and WMVII CP.
Figure 7A:
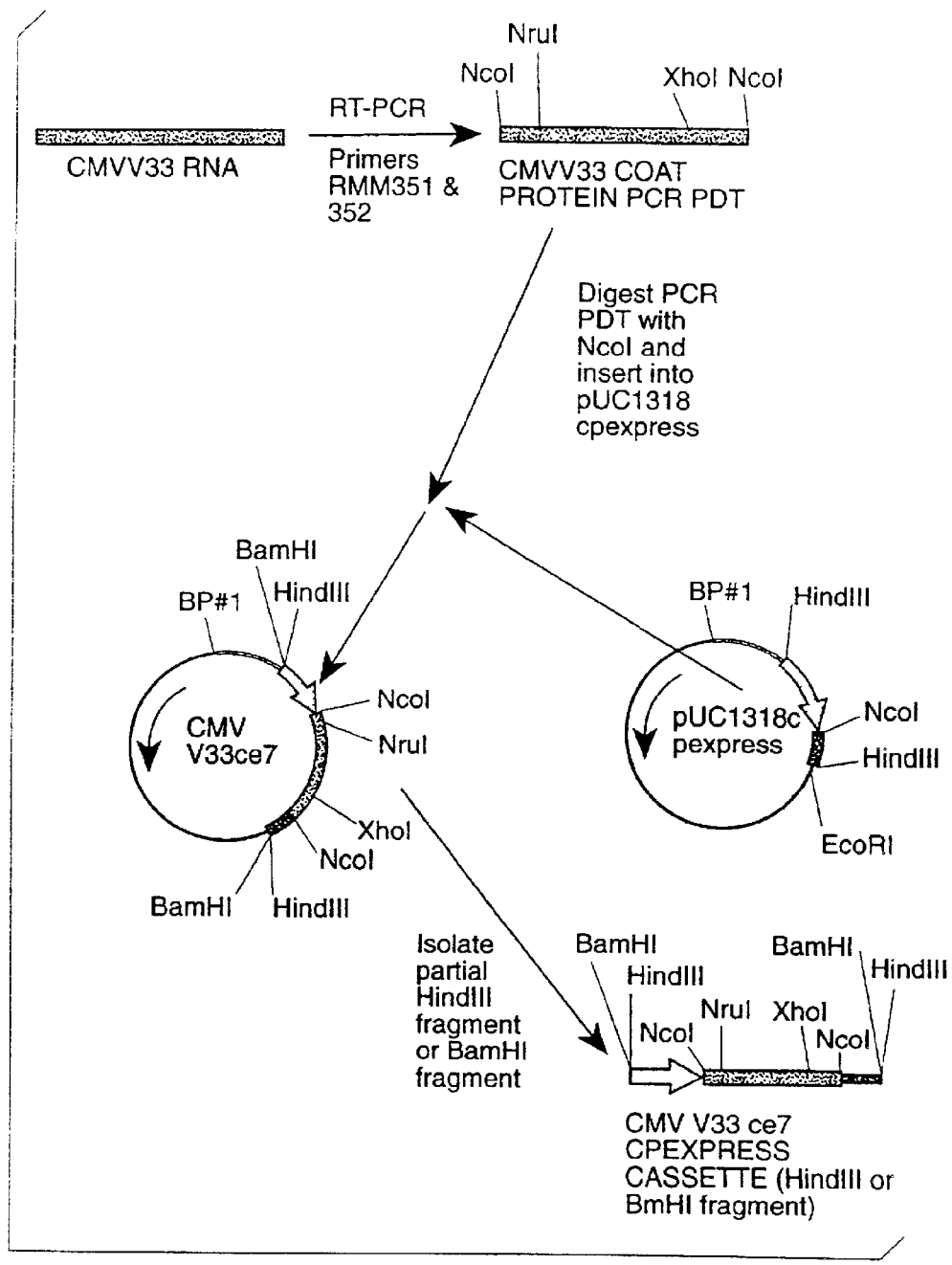
FIG. 7A. Assembly of CMV-V33 CP expression cassette. PRC products of CMV-V33 CP were installed into pUC1318cpexpress by routine methods.
Figure 7B:
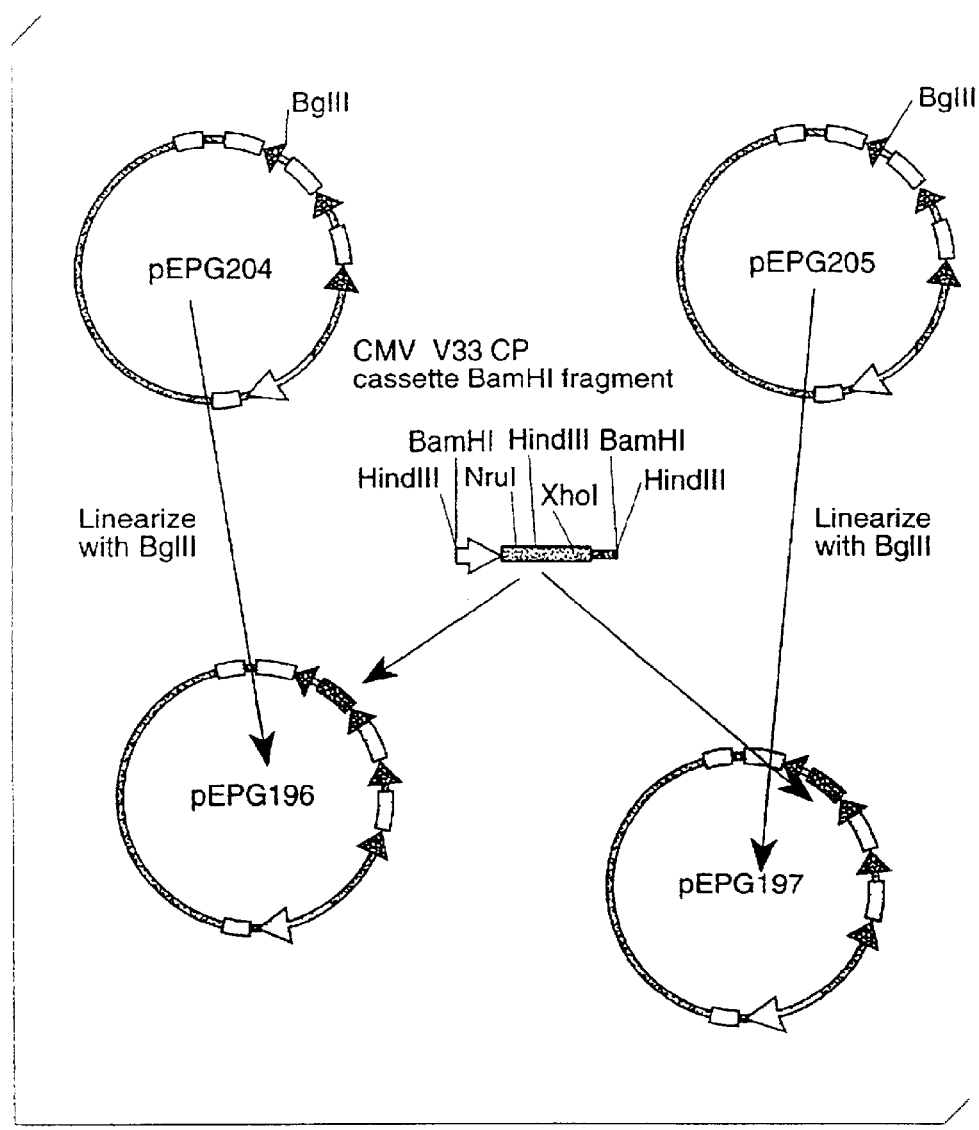
FIG. 7B.
Figure 7C:
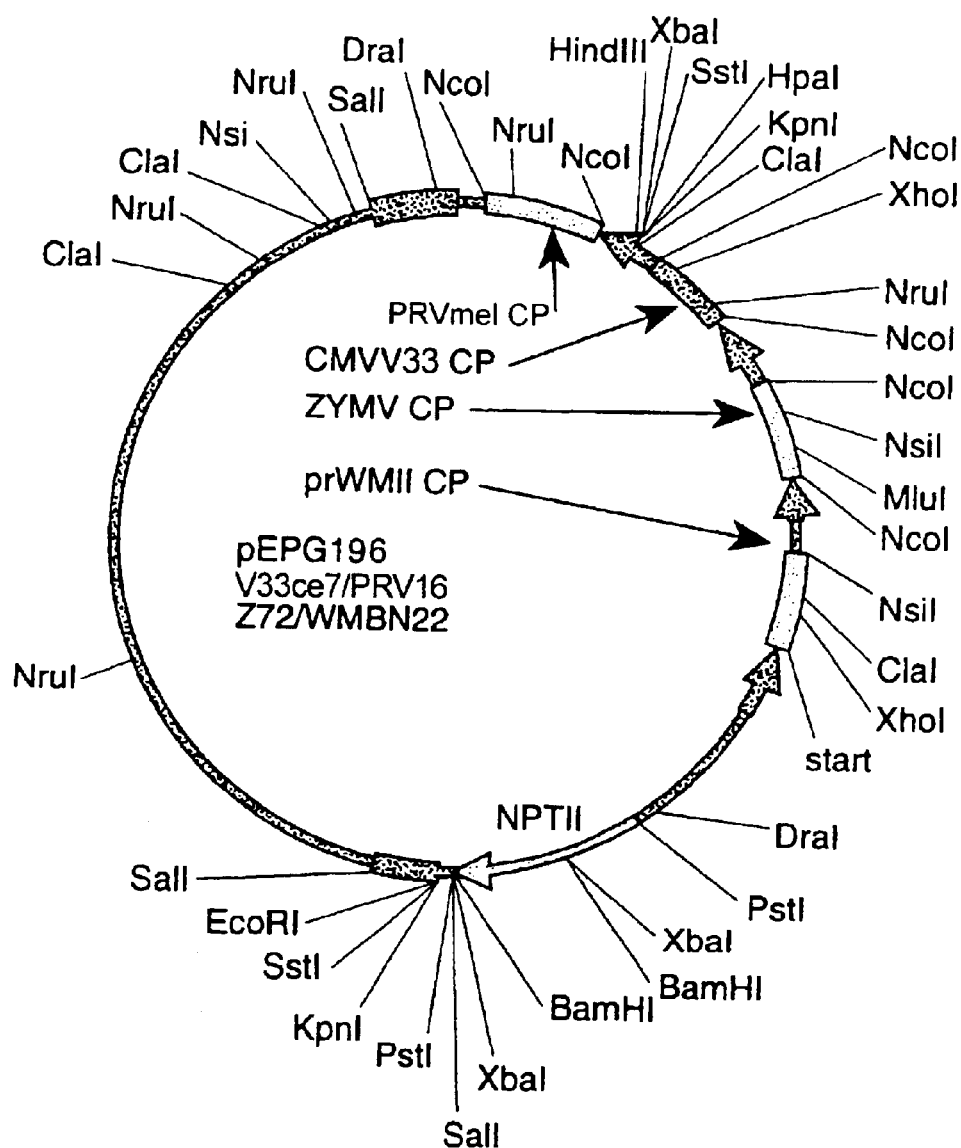
FIG. 7C. Restriction map of pEPG196. This binary plasmid includes the CP expression cassettes for PRV (melon, long), CMV-V33 CP, ZYMV CP, and WMVII. Arrows indicate CaMV-35S promoter fragments.
Figure 7D:
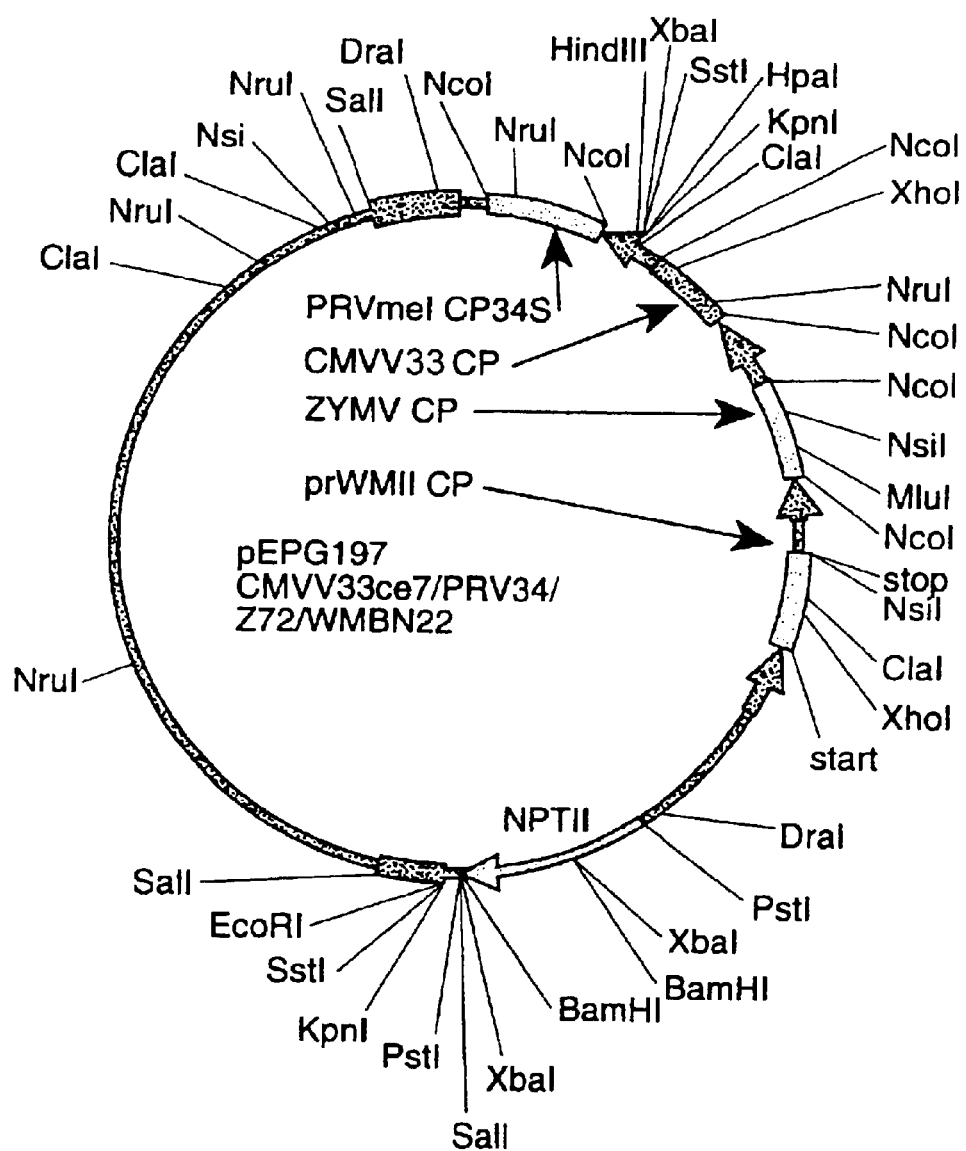
FIG. 7D. Restriction map of pEPG197. This binary plasmid includes the CP expression cassettes for PRV (melon, short), CMV-V33 CP, ZYMV CP, and WMVII CP.

FIGS. 6 and 7 are presented to illustrate the constructions of this invention.

EXAMPLE 1

A. Isolation of CMV RNAs

Zucchini squash plants (20-day old) were inoculated with CMV strains V27, V33, or V34; after 7–10 days, infected leaves were harvested and CMV virus particles were isolated. The procedure used was based on IBM protocols from Lot et al., Annals of Phytopathology, 4:25 (1972), Francki et al., CMI/AAB DESCRIPTIONS OF PLANT VIRUSES, (July, 1979), and Habili and Francki, Virology, 57:292 (1974). Approximately 100 grams (g) of fresh leaves were extracted in an equal weight per volume (w/v) of 0.5 molar (M) Na-citrate (pH 6.5) containing 5 millimolars (mM) EDTA and 100 milliliters (ml) of chloroform. After centrifugation of the extract at 12,000×G for 10 minutes, polyethyleneglycol ("PEG", Sigma Chemical Co. PEG-8000, average molecular weight, Research Grade) was added to the supernatant to a final concentration of 10% and the suspension was stirred for 30–40 minutes at 0–4° C. This suspension was centrifuged at 12,000×G for 10 minutes, and the pellet was resuspended in 40–50 ml of 5 mM Na-borate buffer (pH 9.0) containing 0.5 M EDTA. TRITON X-100 was then added to the virus particle suspension to a final concentration of 2% and stirred on ice for 30 minutes. This suspension was then centrifuged at 19,000×G for 15 minutes, and the supernatant was collected and subsequently centrifuged at 105,000×G for 2 hours. The virus pellet was collected and resuspended in about 2 ml of 5 mM Na-borate buffer (pH 9.0) containing 0.5 mM EDTA. The resuspended virus preparation was applied onto a step sucrose gradient consisting of 5 layers: 5%, 10%, 15%, 20%, and 25% sucrose dissolved in 2.0 mM Na-phosphate buffer (pH 7.5). Gradients were centrifuged at 37,000 rpm in a Sorvall TH641 swinging bucket rotor for 45 minutes. After centrifugation, the virus band was harvested, the virus preparation was dialyzed against Na-borate buffer, and LiCl was added (2 M final concentration) to lyse the virions and to precipitate viral RNA. CMV RNA was dissolved and reprecipitated with ethanol and dissolved in water. By agarose gel electrophoresis, the expected four RNA species were observed.

B. Cloning CMV Coat Protein Genes (a) CMV-V27

The first cDNA strand of CMV-V27 was synthesized with the use of Perkin-Elmer RT-PCR kit reagents and the primer RMM352 (shown in FIG. 4); immediately in the same reaction tube, a PCR was carried out with the use of oligonucleotide primers RMM351 and RMM352 (shown in FIG. 4), following the manufacturer's protocol. The ATG translation start is included in the NcoI site present in primer RMM351. Individual PCR product molecules were cloned using the TA Cloning™ kit (Invitrogen Corp., San Diego, Calif.) into pCRII (included in the TA Cloning™ kit as a linearized plasmid with single 3' dT overhangs at the ends of the molecule). Three clones were isolated for further study: CMVV27TA21, CMVV27TA23, and CMVV27TA26. With the use of a kit (Sequenase 2 purchased from USB, Cleveland, Ohio), the CMV-V27 insert in clone CMVV27TA21 was sequenced.

The coat protein sequence of CMV-V27 was compared to the coat protein sequence from 12 different CMV isolates: CMV-BAUL, CMV-Q3, CMV-WL, CMV-TRK7, CMV-FC, CMV-IL7F, CMV-C, CMV-PR50, CMV-P6, CMV-O, CMV-M and CMV-Y. CMV-V27 CP is similar to CMV-Y CP in that it contains a serine at position 29 while other strains have an alanine at this position. However, CMV-Y CP contains a leucine at position 18 while CMV-V27 CP contains a proline at position 18. In addition, CMV-V27 CP has a methionine at position 206, no other CMV coat proteins have a methionine at this position (Baulcombe, D., "Mutational analysis of CMV RNA3: Effects on RNA3 accumulation, RNA4 synthesis and plant infection." Unpublished Direct Submission. Submitted (19 Jun. 1992) David Baulcombe, The Sainsbury Laboratory, Norwich Research Park, Colney Lane, Norwich, NR2 7UH, United Kingdom; Hayakawa et al., Gene, 71:107 (1988); Hayakawa et al., J. Gen. Virol. 70:499 (1989); Owen et al., J. Gen. Virol., 71:2243 (1990); Pappu et al., "The nucleotide and the deduced amino acid sequences of CP genes of three Puerto Rican isolates of CMV." Unpublished (1992). This sequence is included in the Geneank sequence data base; Salanki et al., "Complete nucleotide sequence of RNA 3 from CMV strain Trk 7." Unpublished (1993). This sequence is included in the GeneBank data base; Shintaku, J. Gen. Virol. 72:2587 (1991)).

(b) CMV-V33

CMV-V33 was purified and viral RNA extracted from a virion preparation as described above; subsequently single stranded cDNA was synthesized using Perkin-Elmer RT-PCR kit reagents and oligomer primer RMM352. The CP gene of strain V33 was amplified using PCR as described above for V27 with the use of oligomer primers RMM351 and RMM352 (FIG. 4). The V33 CP gene PCR product was digested with NcoI and directly cloned into the expression cassette cpexpress installed into pUC1318 (see Kay and McPherson, Nucleic Acids Research, 15:2779 (1987) for pUC1318; Slightom, Gene, 100:251 (1991) for cpexpress; pUC1318cpexpress is the cpexpress described in Slightom, however it is installed into the HindIII site of the modified pUC plasmid pUC1318 described in detail in Kay and McPherson), rather than into the intermediate vector pCRII. By colony hybridization with a CMV CP probe, a number of clones were identified for further analysis: V33cel, V33ce2, V33ce7, and V33ce9. The CMV-V33 insert in clone V33ce7 was sequenced with the use of a kit (Sequenase 2 purchased from USB, Cleveland, Ohio).

The coat protein sequence of CMV-V33 was compared to the coat protein sequence from 13 different CMV isolates:

CMV-BAUL, CMV-Q3, CMV-WL, CMV-TRK7, CMV-FC, CMV-IL7F, CMV-C, CMV-PR50, CMV-V27, CMV-P6, CMV-O, CMV-M and CMV-Y, CMV-V33 CP has a serine at position 67 while all other CMV strains compared included a proline at this position. At position 196, both CMV-V33 CP and CMV-Y CP have a valine residue; all other CMV isolates contains isoleucine at this position. However, at position 184, CMV-V33 CP has an alanine residue while CMV-Y has a threonine residue. Therefore, CMV-V33 CP is unique (Baulcombe, D., "Mutational analysis of CMV RNA3: Effects on RNA3 accumulation, RNA4 synthesis and plant infection." Unpublished Direct Submission. Submitted (19 Jun. 1992) David Baulcombe, The Sainsbury Laboratory, Norwich Research Park, Colney Lane, Norwich, NR2 7UH, United Kingdom; Hayakawa et al., *Gene*, 71:107 (1988); Hayakawa et al., *J. Gen. Virol.* 70:499 (1989); Owen et al., *J. Gen. Virol.*, 1:2243(1990); Pappu et al., "The nucleotide and the deduced amino acid sequences of coat protein genes of three Puerto Rican isolates of cucumber mosaic virus." Unpublished (1992). This sequence is included in the GeneBank sequence data base; Salanki et al., "Complete nucleotide sequence of RNA 3 from cucumber mosaic virus strain Trk 7." Unpublished (1993). This sequence is included in the GeneBank data base; Shintaku, *J. Gen. Virol.* 72:2587 (1991)).

(c) CMV-V34

CMV-V34 RNA was prepared as described above. Subsequently, the first cDNA strand was synthesized using CMV-V34 template in a reaction that included the following: approximately 2 µg CMV-V34 RNA, 1×buffer for Superscript Reverse Transcriptase (supplied by BRLGIBCO, Grand Island, N.Y.), 2 mM dNTPs, oligomer primer RMM352 (37.5 µg/ml), 1.5 microliters (µl) RNasin, and 1 Al Superscript Reverse Transcriptase (BRL-GIBCO) in a 20-µl reaction. After this reaction was allowed to proceed for 30 minutes, an aliquot of the first strand reaction was used as a template in a PCR to amplify the CMV-V34 CP gene. The CMV-V34 CP gene PCR product was cloned into the pCRII vector included in the TA Cloning' Kit supplied by InvitrogenCorp. Two clones were isolated for further study: TA17V34 and TA112V34. The CMV-V34 insert of clone TA17V34 was sequenced with the use of a kit (Sequenase 2 purchased from USB, Cleveland, Ohio). Comparative sequence analysis of the CMV-V34 CP gene with other CMV CP genes CMV-BAUL., CMV-Q3, CMV-WL, CMV-TRK7, CMV-FC, CMV-IL7F, CMV-C, CMV-PR50, CMV-V27, CMV-P6, CMV-O, CMV-M and CMV-Y showed that the CMV-V34 CP gene is unique (Baulcombe, D. Mutational analysis of CMV RNA3: Effects on RNA3 accumulation, RNA4 synthesis and plant infection. Unpublished Direct Submission. Submitted (19 Jun. 1992) David Baulcombe, The Sainsbury Laboratory, Norwich Research Park, Colney Lane, Norwich, NR2 7UH, United Kingdom; Hayakawa et al., *Gene*, 71:107 (1988); Hayakawa et al., *J. Gen. Virol.* 70:499 (1989); Owen et al., *J. Gen. Virol.*, 71:2243 (1990); Pappu et al., (1992) "The nucleotide and the deduced amino acid sequences of coat protein genes of three Puerto Rican isolates of cucumber mosaic virus." Unpublished. This sequence is included in the GeneBank sequence data base; Salanki et al., "Complete nucleotide sequence of RNA 3 from cucumber mosaic virus strain Trk 7." Unpublished (1993) This sequence is included in the GeneBank data base; Shintaku, *J. Gen. Virol.* 72:2587 (1991)).

C. Engineering CMV CP Genes (a) CMV-V27

The NcoI fragment in CMVV27TA21 that harbors CMV-V27 CP coding sequences was excised from CMVV27TA21 and inserted into the plant expression cassette cpexpress in pUC18 to give CMVV27TA21ce42. The resulting expression cassette was isolated as a partial HindIII fragment and inserted into the binary vector pGA482G [The parent binary plasmid was pGA482, constructed by An (Plant Physiol., 81:86 (1986)). This binary vector contains the T-DNA border sequences from pTiT37, the selectable marker gene NOS-NPTII (which contains the plant-expressible nopaline gene promoter fused to the bacterial NPTII gene obtained from Tn5), a multiple cloning region, and the cohesive ends of phage lambda (An, Plant Physiol., 81:86 (1986))] to yield pEPG191 and pEPG192. Subsequently, a PRV CP expression cassette was installed to obtain a binary vector that included both CMV-V27 CP and PRV CP expression cassettes.

Alternatively, the CMV-V27 CP NcoI fragment obtained from CMVV27TA21 was installed into pUC1318cpexpress (see Kay et al., Nucleic Acids Research, 15:2779 (1987) for pUC1318; Slightom, Gene 100:251 (1991) for cpexpress; pUC1318cpexpress is the cpexpress described in Slightom, however it is installed into the HindIII site of the modified pUC plasmid pUC 1318 described in detail in Kay et al.) to give the plasmid CMVV27TA210E13 (similar to CMVV27TA21ce42). The plasmid pUC1318 provided additional sites (e.g., BamHI and XbaI) with which the cassette could be inserted into the binary vector pGA482G. Subsequently, the bacteria-derived gentamicin-(3)-N-acetyl-transferase gene (Allmansberger et al., Mol. Gen. Genet., 198:514 (1985)) was installed into a SalI site outside of the T-DNA region, adjacent to the left border ($B_L$)). The BamHI fragment harboring the CMV-V27 CP expression cassette was isolated and inserted into the BglII site of the binary plasmid pEPG205 (PRV34/Z72/WMBN22) to give pEPG240 (CMVV27/PRV34/Z72/WMBN22). The BamHI fragment was also installed into the BglII site of the binary plasmid pEPG204 (PRV16/Z72/WMBN22) to yield pEPG239 (CMVV2716/PRV16/Z72/WMBN22) (Table 1). For further information on PRV CP genes, refer to Applicants' International Patent Application No. PCT/US95/07272 entitled "Papaya Ringspot Virus Coat Protein Gene" filed on Jun. 7, 1995, incorporated by reference herein. For further information on ZYMV and WMV-2 CP genes, refer to Applicants' International Patent Application No. PCT/US89/03094 filed on Jul. 20, 1989 entitled "Potyvirus Coat Protein Genes and Plants Transformed Therewith", incorporated by reference herein.

TABLE 1

| Binary | Parental Plasmid | Site | CMVcn Cassette | pEPG# |
|---|---|---|---|---|
| pGA482G | pGA482G | Hindi= | CMVV27cpexpress | 191 or 192 |
| pPRBN | pEPG204(P16sZW) | BglII | CMVV27cpexpress | 239 |
| pPRBN | pEPG2045 (P16sZW) | BglII | CMVV27cpexpress | 240 |
| pPRBN | pEPG106(ZW) | Hindi= | CMVV27cpexpress | 243 |
| pGA482G | pGA482G | Hindi= | CMVV33ce7 | 198 |
| pPRBN | pEPG106(ZW) | Hindi= | CMVV33ce7 | 244 |
| pPRBN | pEPG204(P16sZW) | BglII | CMVV33ce7 | 196 |
| pPRBN | pEPG205(P34sZW) | BglII | CMVV33ce7 | 197 |
| pGA482G | pGA482G | Hindi= | 17V34cpexp113 | 190 |

(b) CMV-V33

Subsequently, both HindIII and BamHI fragments were excised from clone V33ce7; these fragments carried the complete expression cassette for CMV-V33 CP gene. The BamHI fragment (V33 CP expression cassette) was inserted into the BglII site of pEPG204 PRV16/ZY72MMBN22) to obtain pEPG196. The BamHI fragment was also inserted into the BglII site of pPEPG205 (PRV34/ZY72/WMBN22) to obtain pEPG197 (V3329/PRV34/ZY72/WMBN22). The HindIII fragment harboring the V33 CP cassette was installed into pGA482G to obtain pEPG198 (Table 1).

(c) CMV-V34

An NcoI fragment excised from clone TA17V34 was installed into the NcoI site of pUC1318 cpexpress. A resulting plasmid that includes the CMV-V34 coding NcoI fragment inserted in the sense orientation is 17V34/cpexp113. A partial HindIII fragment from the plasmid 17V34/cpexp113 was isolated and installed into pGA482G to yield pEPG190 (Table 1).

(d) Agrobacterium Strains

The binary plasmids described here, such as pPRBN (for further information on these plasmids, refer to Applicants' International Patent Application No. PCT/US95/06261 entitled "Transgenic Plants Expressing DNA Constructs Containing a Plurality of Genes to Impart Virus Resistance" filed on Jun. 7, 1995, incorporated by reference herein) or their derivatives, can be transferred into Agrobacterium strains A208, C58, LBA4404, C58Z707, A4RS, A4RS (pRi278b), Mog301 and others. Strains A208, C58, LBA4404, and A4RS are available from ATCC, 12301 Parklawn Drive, Rockville, Md. A4RS (pRi278b) was obtained from Dr. F. Casse-Delbart, C.N.R.A., Route de Saint Cyr, F78000, Versailles, France. C58Z707 was obtained from Dr. A. G. Hepburn, University of Illinois, Urbana, Ill. Mog301 was obtained from Mogen Nev., Leiden, Netherlands.

D. Transfer of CMV Coat Protein Genes to Tobacco

In order to test whether the CMV CP gene constructs described herein confcr protection against CMV challenge with homologous strains, some of the binary plasmids listed above (e.g., pEPG197, pEPG198, pEPG239, and pEPG240) have been used to insert these novel CMV CP genes into *Nicotiana tabacum*. Agrobacterium-mediated transfer of the plant expressible CMV CP genes described herein was done using the methods described in PCT published application WO 89/05859, entitled "Agrobacterium Mediated Transformation of Germinating Plant Seeds.

Five $R_1$ progeny lines of *Nicotiana t.* transformed with 35 the binary plasmid pEPG239 and five $R_1$ progeny lines of *Nicotiana t.* transformed with the binary plasmid pEPG240 have been obtained. These binary plasmids include the CP gene of CMV-V27. The ten $R_o$ parental plants of these lines were assayed for NPTII protein expression by ELISA. They each expressed NPT II protein by ELISA. Furthermore, these ten lines were assayed for both the nptII and CMV-V27 CP genes by PCR analysis. PCR analysis detected both genes in all ten Ro plants.

The binary plasmid pEPG198 was used to obtain 11 $R_0$ transgenic *Nicotiana t.* plants. By PCR analysis, the CMV-V33 CP gene was detected in nine of the eleven $R_0$ plants tested.

E. Cloning and Engineering CMV-A35 PC Gene 20-day-old zucchini squash plants in the greenhouse were inoculated with CMV-A35; after 7–10 days infected leaves were harvested. Total RNA was isolated from these infected plants by the use of Tri-Reagent and the instructions provided with the reagent (Molecular Research Center, Inc., Cincinnati, Ohio). Single-stranded cDNA was synthesized using total RNA template. The reaction included 1× first Strand cDNA Synthesis Buffer (GIBCO-BRL), 1 mM dNTP's (Pharmacia), 2 μl oligonucleotide primer RMM352 (150 μg/ml), 2 μl RNasin (Promega), and 1 μl RTase Superscript II (GIBCO-BRL) in a 20 μl reaction volume. The CMV-A35 CP gene was PCR amplified with the use of CMV CP-specific primers RMM351 and 352. The PCR included 3 μl of the cDNA synthesis reaction described above, 8 μl of each primer RMM351 and RMM352 (150 μg/μl stock), 5 μl 10× reaction buffer, 4 μl dNTP's (10 mM), 1.5 μl $MgCl_2$ (50 mM), and 0.5 μl, Taq polymerase (BRL-GIBCO). PCR conditions were carried out as follows: 93° 45 sec, 50° 45 sec, then 72° 180 sec for 30 cycles, then 72° for 5 min, then. hold at 4°. PCR products were visualized by agarose gel electrophoresis and subsequently cloned. PCR product molecules were cloned into the pCRII vector supplied with the TA cloning kit (Invitrogen Corp.) Four clones were identified and restriction mapped, however, none were sequenced for further analysis.

Alternatively, an aliquot of the CMV-A35 PCR product was digested with NcoI and ligated it into the NcoI site of pUC19B2 cpexpress to give the plasmid CMV-A35cpexp33. The CP insert of this plasmid was sequenced with the use of the Sequenase II Kit supplied by USBiochemical (FIG. 8). Sequence analysis reveals that CMV-A35 CP sequence differs from the CP sequences of CMV-C, CMV-V27, CMV-V33, CMV-V34, and CMV-WL (FIGS. 9 and 10). For example, A35 differs from the other CMV-C strains referred to above at amino acid position #26 (FIG. 9). Examination of the nucleotide sequence comparisons differs from other CMV CP genes characterized (FIG. 10).

A BamHI/BlIII fragment was excised from A35cpexp33 and installed into the unique BglII site pGA482G. The plasmid pUC19B2cpexp provides a BamHI site at the 5' end of the cpexp cassette and a BglII site at the 3' end of the expression cassette. Upon insertion into a BglII site, the unique BglII site of the binary plasmid pGA482 is maintained for subsequent insertions of gene cassettes. Binary plasmids that include the CMV-A35 expression cassette are being transformed into various *Agrobacterium* strains (e.g., C58Z707, Mog301, and LBA4404). These *Agrobacterium* strains are used to transform plants to impart resistance to CMV CARNA5.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An isolated and purified DNA molecule comprising DNA encoding the coat protein of the V34 strain of cucumber mosaic virus.

2. The isolated and purified DNA molecule of claim 1 wherein the DNA molecule comprises the nucleotide sequence shown in SEQ ID NO:5.

3. A vector comprising a chimeric expression cassette comprising the DNA molecule of claim 1, a promoter and a polyadenylation signal, wherein the promoter is operably linked to the DNA molecule, and the DNA molecule is operably linked to the polyadenylation signal.

4. The vector of claim 3, wherein the promoter is the cauliflower mosaic virus 35S promoter.

5. The vector of claim 4 wherein the polyadenylation signal is the polyadenylation signal of the cauliflower mosaic 35S gene.

6. A bacterial cell comprising the vector of claim 3.

7. The bacterial cell of claim 6 wherein the bacterial cell is selected from the group consisting of an *Agrobacterium tumefaciens* and an *Agrobacterium rhizogenes* cell.

8. A transformed plant cell transformed with the vector of claim 3.

9. The transformed plant cell of claim 8 wherein the promoter is cauliflower mosaic virus 35S promoter and the polyadenylation signal is the polyadenylation signal of the cauliflower mosaic 35S gene.

10. A plant selected from the family *Cucurbitaceae* comprising a plurality of the transformed cells of claim 8.

11. A plant selected from the family *Solanaceae* comprising a plurality of the transformed cells of claim 8.

12. A method of preparing a cucumber mosaic viral resistant plant comprising:

transforming plant cells with a chimeric expression cassette comprising a promoter functional in plant cells operably inked to a DNA molecule that encodes a coat protein; wherein the DNA molecule is from cucumber mosaic virus strain V34; regenerating the plant cells to provide a differentiated plant; and identifying a transformed plant that expresses the cucumber mosaic virus coat protein at a level sufficient to render the plant resistant to infection by cucumber mosaic virus strain V34.

13. The method of claim 12 wherein the plant is a dicot.

14. The method of claim 13 wherein the dicot is selected from the family *Cucurbitaceae*.

15. The method of claim 13 wherein the dicot is selected from the family *Solanaceae*.

16. A vector comprising a chimeric expression cassette comprising the DNA molecule of claim 1 and at least one chimeric expression cassette comprising a heterologous CMV coat protein gene which is not the coat protein gene of the V34 strain of CMV, a papaya ringspot virus coat protein gene, a zucchini yellow mosaic virus coat protein gene, or a watermelon mosaic virus II coat protein gene, wherein each expression cassette comprises a promoter and a polyadenylation signal, wherein the promoter is operably linked to the DNA molecule or coat protein gene, and the DNA molecule or coat protein gene is operably linked to the polyadenylations signal.

17. A bacterial cell comprising the vector of claim 16.

18. A plant cell transformed with the vector of claim 16.

19. The plant cell of claim 18 wherein the promoter is cauliflower mosaic virus 35S promoter and the polyadenylation signal is the polyadenylation signal of the cauliflower mosaic 35S gene.

20. A plant selected from the family *Cucurbitaceae* comprising a plurality of the transformed cells of claim 18.

21. A plant selected from the family *Solanaceae* comprising a plurality of the transformed cells of claim 18.

* * * * *

UNITED STATES PATENT AND TRADEMARK OFFICE
CERTIFICATE OF CORRECTION

PATENT NO. : 6,849,780 B2  Page 1 of 1
DATED : February 1, 2005
INVENTOR(S) : Maury L. Boeshore et al.

It is certified that error appears in the above-identified patent and that said Letters Patent is hereby corrected as shown below:

Column 43,
Line 22, the word "inked" should be deleted and the word -- linked -- should be added in its place.

Signed and Sealed this

Sixteenth Day of August, 2005

JON W. DUDAS
*Director of the United States Patent and Trademark Office*

SEQUENCE LISTING

```
<160> NUMBER OF SEQ ID NOS: 21

<210> SEQ ID NO 1
<211> LENGTH: 772
<212> TYPE: DNA
<213> ORGANISM: cucumber mosaic virus - V27
```

<220> FEATURE:
<221> NAME/KEY: CDS
<222> LOCATION: (3)..(656)

<400> SEQUENCE: 1

```
cc atg gac aaa tct gaa tca acc agt gct ggt cgt aac cgt cgg cgt          47
   Met Asp Lys Ser Glu Ser Thr Ser Ala Gly Arg Asn Arg Arg Arg
   1               5                   10                  15 cgt ccg cgt cgt ggt tcc cgc tcc gcc tcc tcc tcg gat gct aac             95
Arg Pro Arg Arg Gly Ser Arg Ser Ala Ser Ser Ser Ser Asp Ala Asn
                20                  25                  30 ttt aga gtc ttg tcg cag cag ctt tcg cga ctt aac aag acg tta gca        143
Phe Arg Val Leu Ser Gln Gln Leu Ser Arg Leu Asn Lys Thr Leu Ala
            35                  40                  45 gct ggt cgt cca act att aac cac cca acc ttt gta ggg agt gaa cgc        191
Ala Gly Arg Pro Thr Ile Asn His Pro Thr Phe Val Gly Ser Glu Arg
        50                  55                  60 tgt aaa cct ggg tac acg ttc aca tct att acc cta aag cca cca aaa        239
Cys Lys Pro Gly Tyr Thr Phe Thr Ser Ile Thr Leu Lys Pro Pro Lys
    65                  70                  75 ata gac cgt ggg tct tat tac ggt aaa agg ttg tta tta cct gat tca        287
Ile Asp Arg Gly Ser Tyr Tyr Gly Lys Arg Leu Leu Leu Pro Asp Ser
80                  85                  90                  95 gtc acg gaa tat gat aag aag ctt gtt tcg cgc att caa att cga gtt        335
Val Thr Glu Tyr Asp Lys Lys Leu Val Ser Arg Ile Gln Ile Arg Val
                100                 105                 110 aat cct ttg ccg aaa ttt gat tct acc gtg tgg gta aca gtc cgt aaa        383
Asn Pro Leu Pro Lys Phe Asp Ser Thr Val Trp Val Thr Val Arg Lys
            115                 120                 125 gtt cct gcc tcc tcg gac tta tcc gtt gcc gcc atc tct gct atg ttc        431
Val Pro Ala Ser Ser Asp Leu Ser Val Ala Ala Ile Ser Ala Met Phe
        130                 135                 140 gcg gac gga gcc tca ccg gta ctg gtt tat cag tat gct gca tct gga        479
Ala Asp Gly Ala Ser Pro Val Leu Val Tyr Gln Tyr Ala Ala Ser Gly
    145                 150                 155 gtc caa gct aac aac aaa ttg ttg tat gat ctt tcg gcg atg cgc gct        527
Val Gln Ala Asn Asn Lys Leu Leu Tyr Asp Leu Ser Ala Met Arg Ala
160                 165                 170                 175 gat ata ggt gac atg aga aag tac gcc gtc ctc gtg tat tca aaa gac        575
Asp Ile Gly Asp Met Arg Lys Tyr Ala Val Leu Val Tyr Ser Lys Asp
                180                 185                 190 gat gcg ctc gag acg gac gag cta gta ctt cat gtt gac atc gag cac        623
Asp Ala Leu Glu Thr Asp Glu Leu Val Leu His Val Asp Ile Glu His
            195                 200                 205 caa cgt att ccc acg tct ggg atg ctc cca gtc tgattccgtg ttcccagaac      676
Gln Arg Ile Pro Thr Ser Gly Met Leu Pro Val
        210                 215 cctccctccg atttctgtgg cgggagctga gttggcagtt ctgctataaa ctgtctgaag      736
tcactaaacg tttcacggtg aacgggttgt ccatgg                                772
```

<210> SEQ ID NO 2
<211> LENGTH: 218
<212> TYPE: PRT
<213> ORGANISM: cucumber mosaic virus - V27

<400> SEQUENCE: 2

```
Met Asp Lys Ser Glu Ser Thr Ser Ala Gly Arg Asn Arg Arg Arg
1               5                   10                  15

Pro Arg Arg Gly Ser Arg Ser Ala Ser Ser Ser Ser Asp Ala Asn Phe
                20                  25                  30
```

```
Arg Val Leu Ser Gln Gln Leu Ser Arg Leu Asn Lys Thr Leu Ala Ala
         35                  40                  45

Gly Arg Pro Thr Ile Asn His Pro Thr Phe Val Gly Ser Glu Arg Cys
 50                  55                  60

Lys Pro Gly Tyr Thr Phe Thr Ser Ile Thr Leu Lys Pro Pro Lys Ile
 65                  70                  75                  80

Asp Arg Gly Ser Tyr Tyr Gly Lys Arg Leu Leu Leu Pro Asp Ser Val
                 85                  90                  95

Thr Glu Tyr Asp Lys Lys Leu Val Ser Arg Ile Gln Ile Arg Val Asn
                100                 105                 110

Pro Leu Pro Lys Phe Asp Ser Thr Val Trp Val Thr Val Arg Lys Val
            115                 120                 125

Pro Ala Ser Ser Asp Leu Ser Val Ala Ala Ile Ser Ala Met Phe Ala
            130                 135                 140

Asp Gly Ala Ser Pro Val Leu Val Tyr Gln Tyr Ala Ala Ser Gly Val
145                 150                 155                 160

Gln Ala Asn Asn Lys Leu Leu Tyr Asp Leu Ser Ala Met Arg Ala Asp
                165                 170                 175

Ile Gly Asp Met Arg Lys Tyr Ala Val Leu Val Tyr Ser Lys Asp Asp
                180                 185                 190

Ala Leu Glu Thr Asp Glu Leu Val Leu His Val Asp Ile Glu His Gln
            195                 200                 205

Arg Ile Pro Thr Ser Gly Met Leu Pro Val
        210                 215

<210> SEQ ID NO 3
<211> LENGTH: 792
<212> TYPE: DNA
<213> ORGANISM: cucumber mosaic virus - V33
<220> FEATURE:
<221> NAME/KEY: CDS
<222> LOCATION: (3)..(656)

<400> SEQUENCE: 3 cc atg gac aaa tct gaa tca acc agt gct ggt cgt aac cgt cga cgt      47
   Met Asp Lys Ser Glu Ser Thr Ser Ala Gly Arg Asn Arg Arg Arg
    1               5                  10                  15 cgt ccg cgt cgt ggt tcc cgc tcc gcc ccc tcc tcc gcg gat gcc aac     95
Arg Pro Arg Arg Gly Ser Arg Ser Ala Pro Ser Ser Ala Asp Ala Asn
                 20                  25                  30 ttt aga gtc ttg tcg cag cag ctt tcg cga ctt aat aag acg ttg tca    143
Phe Arg Val Leu Ser Gln Gln Leu Ser Arg Leu Asn Lys Thr Leu Ser
             35                  40                  45 gct ggt cgt cca act att aac cac cca acc ttt gta ggg agt gag cgt    191
Ala Gly Arg Pro Thr Ile Asn His Pro Thr Phe Val Gly Ser Glu Arg
 50                  55                  60 tgt aaa tct ggg tac acg ttc aca tct att acc cta aag ccg ccg aaa    239
Cys Lys Ser Gly Tyr Thr Phe Thr Ser Ile Thr Leu Lys Pro Pro Lys
 65                  70                  75 ata gac cgt ggg tct tat tat ggt aaa agg ttg tta tta cct gat tca    287
Ile Asp Arg Gly Ser Tyr Tyr Gly Lys Arg Leu Leu Leu Pro Asp Ser
 80                  85                  90                  95 gtc aca gaa tat gat aag aaa ctt gtt tcg cgc att caa att cga gtt    335
Val Thr Glu Tyr Asp Lys Lys Leu Val Ser Arg Ile Gln Ile Arg Val
                100                 105                 110 aat ccc ttg ccg aaa ttt gat tct acc gtg tgg gtg aca gtc cgt aaa    383
Asn Pro Leu Pro Lys Phe Asp Ser Thr Val Trp Val Thr Val Arg Lys
            115                 120                 125
```

```
gtt cct gcc tcc tcg gac tta tcc gtt gcc gcc atc tct gct atg ttt    431
Val Pro Ala Ser Ser Asp Leu Ser Val Ala Ala Ile Ser Ala Met Phe
        130                 135                 140 gcg gac gga gcc tca ccg gta ctg gtt tat cag tac gct gca tct gga    479
Ala Asp Gly Ala Ser Pro Val Leu Val Tyr Gln Tyr Ala Ala Ser Gly
    145                 150                 155 gtc caa gct aac aac aaa ttg ttg tat gat ctt tcg gcg atg cgc gct    527
Val Gln Ala Asn Asn Lys Leu Leu Tyr Asp Leu Ser Ala Met Arg Ala
160                 165                 170                 175 gat ata ggc gac atg aga aag tac gcc gtc ctc gtg tat tca aaa gac    575
Asp Ile Gly Asp Met Arg Lys Tyr Ala Val Leu Val Tyr Ser Lys Asp
        180                 185                 190 gat gca ctc gag acg gac gag cta gta ctt cat gtt gac gtc gag cac    623
Asp Ala Leu Glu Thr Asp Glu Leu Val Leu His Val Asp Val Glu His
    195                 200                 205 caa cgc att ccc acg tct ggg gtg ctc cca gta taattctgtg ctttccagaa  676
Gln Arg Ile Pro Thr Ser Gly Val Leu Pro Val
        210                 215 ccctccctcc gatttctgtg gcgggagctg agttggcagt tctgctgtaa actgtctgaa  736
gtcactaaac gttttacggt gaacgggttg tccatgggtt tcggttttt tgttaa       792

<210> SEQ ID NO 4
<211> LENGTH: 218
<212> TYPE: PRT
<213> ORGANISM: cucumber mosaic virus - V33

<400> SEQUENCE: 4

Met Asp Lys Ser Glu Ser Thr Ser Ala Gly Arg Asn Arg Arg Arg Arg
1               5                   10                  15

Pro Arg Arg Gly Ser Arg Ser Ala Pro Ser Ser Ala Asp Ala Asn Phe
            20                  25                  30

Arg Val Leu Ser Gln Gln Leu Ser Arg Leu Asn Lys Thr Leu Ser Ala
        35                  40                  45

Gly Arg Pro Thr Ile Asn His Pro Thr Phe Val Gly Ser Glu Arg Cys
    50                  55                  60

Lys Ser Gly Tyr Thr Phe Thr Ser Ile Thr Leu Lys Pro Pro Lys Ile
65                  70                  75                  80

Asp Arg Gly Ser Tyr Tyr Gly Lys Arg Leu Leu Leu Pro Asp Ser Val
                85                  90                  95

Thr Glu Tyr Asp Lys Lys Leu Val Ser Arg Ile Gln Ile Arg Val Asn
            100                 105                 110

Pro Leu Pro Lys Phe Asp Ser Thr Val Trp Val Thr Val Arg Lys Val
        115                 120                 125

Pro Ala Ser Ser Asp Leu Ser Val Ala Ala Ile Ser Ala Met Phe Ala
    130                 135                 140

Asp Gly Ala Ser Pro Val Leu Val Tyr Gln Tyr Ala Ala Ser Gly Val
145                 150                 155                 160

Gln Ala Asn Asn Lys Leu Leu Tyr Asp Leu Ser Ala Met Arg Ala Asp
                165                 170                 175

Ile Gly Asp Met Arg Lys Tyr Ala Val Leu Val Tyr Ser Lys Asp Asp
            180                 185                 190

Ala Leu Glu Thr Asp Glu Leu Val Leu His Val Asp Val Glu His Gln
        195                 200                 205

Arg Ile Pro Thr Ser Gly Val Leu Pro Val
    210                 215
```

<210> SEQ ID NO 5
<211> LENGTH: 771
<212> TYPE: DNA
<213> ORGANISM: cucumber mosaic virus - V34
<220> FEATURE:
<221> NAME/KEY: CDS
<222> LOCATION: (3)..(656)

<400> SEQUENCE: 5

```
cc atg gac aaa tct gaa tca acc agt gct ggt cgt aac cgt cga cgt       47
   Met Asp Lys Ser Glu Ser Thr Ser Ala Gly Arg Asn Arg Arg Arg
   1               5                  10                  15 cgt ccg cgt cgt ggt tcc cgc tcc gct tcc tcc tct tcg gat gct aac       95
Arg Pro Arg Arg Gly Ser Arg Ser Ala Ser Ser Ser Ser Asp Ala Asn
                20                  25                  30 ttt aga gtc ttg tcg cag cag ctt tcg cga ctt aac aag acg tta gca      143
Phe Arg Val Leu Ser Gln Gln Leu Ser Arg Leu Asn Lys Thr Leu Ala
                35                  40                  45 gct ggt cgt cca act att aac cac cca acc ttt gta ggg agt gaa cgc      191
Ala Gly Arg Pro Thr Ile Asn His Pro Thr Phe Val Gly Ser Glu Arg
 50                  55                  60 tgt aga cct ggg tac acg ttc aca tct att acc cta aag cca cca aaa      239
Cys Arg Pro Gly Tyr Thr Phe Thr Ser Ile Thr Leu Lys Pro Pro Lys
 65                  70                  75 ata gac cgc ggg tct tac tac ggt aaa agg ttg tta cta cct gat tca      287
Ile Asp Arg Gly Ser Tyr Tyr Gly Lys Arg Leu Leu Leu Pro Asp Ser
 80                  85                  90                  95 gtc acg gaa tat gat aag aag ctt gtt tcg cgc att caa att cga gtt      335
Val Thr Glu Tyr Asp Lys Lys Leu Val Ser Arg Ile Gln Ile Arg Val
                100                 105                 110 aat cct ttg ccg aaa ttt gat tct acc gtg tgg gtg aca gtt cgt aaa      383
Asn Pro Leu Pro Lys Phe Asp Ser Thr Val Trp Val Thr Val Arg Lys
                115                 120                 125 gtt cct gcc tcc tcg gac tta tcc gtt gcc gcc atc tct gct atg ttc      431
Val Pro Ala Ser Ser Asp Leu Ser Val Ala Ala Ile Ser Ala Met Phe
                130                 135                 140 gcg gac gga gcc tca ccg gta ctg gtt tat cag tat gct gca tct gga      479
Ala Asp Gly Ala Ser Pro Val Leu Val Tyr Gln Tyr Ala Ala Ser Gly
145                 150                 155 gtt caa gct aac aac aaa ttg ttg tat gat ctt tcg gcg atg cgc gct      527
Val Gln Ala Asn Asn Lys Leu Leu Tyr Asp Leu Ser Ala Met Arg Ala
160                 165                 170                 175 gat ata ggt gac atg aga aag tac gcc gtc ctc gtg tat tca aaa gac      575
Asp Ile Gly Asp Met Arg Lys Tyr Ala Val Leu Val Tyr Ser Lys Asp
                180                 185                 190 gat gca ctc gag acg gac gag cta gta ctt cat gtt gac atc gag cac      623
Asp Ala Leu Glu Thr Asp Glu Leu Val Leu His Val Asp Ile Glu His
                195                 200                 205 caa cgc att ccc acg tct ggg gtg ctc cca gtt tgattccgtg ttccagaacc    676
Gln Arg Ile Pro Thr Ser Gly Val Leu Pro Val
                210                 215 ctccctccga tttctgtggc gggagctgag ttggcagttc tgctataaac tgtctgaagt    736
cactaaacgt tttacggtga acgggttgtc catgg                               771
```

<210> SEQ ID NO 6
<211> LENGTH: 218
<212> TYPE: PRT
<213> ORGANISM: cucumber mosaic virus - V34

<400> SEQUENCE: 6

-continued

```
Met Asp Lys Ser Glu Ser Thr Ser Ala Gly Arg Asn Arg Arg Arg
1               5                   10                  15

Pro Arg Arg Gly Ser Arg Ser Ala Ser Ser Ser Asp Ala Asn Phe
            20                  25                  30

Arg Val Leu Ser Gln Gln Leu Ser Arg Leu Asn Lys Thr Leu Ala Ala
            35                  40                      45

Gly Arg Pro Thr Ile Asn His Pro Thr Phe Val Gly Ser Glu Arg Cys
50                          55                  60

Arg Pro Gly Tyr Thr Phe Thr Ser Ile Thr Leu Lys Pro Pro Lys Ile
65                  70                  75                  80

Asp Arg Gly Ser Tyr Tyr Gly Lys Arg Leu Leu Pro Asp Ser Val
                85                  90                  95

Thr Glu Tyr Asp Lys Lys Leu Val Ser Arg Ile Gln Ile Arg Val Asn
                100                 105                 110

Pro Leu Pro Lys Phe Asp Ser Thr Val Trp Val Thr Val Arg Lys Val
            115                 120                 125

Pro Ala Ser Ser Asp Leu Ser Val Ala Ala Ile Ser Ala Met Phe Ala
130                 135                     140

Asp Gly Ala Ser Pro Val Leu Val Tyr Gln Tyr Ala Ala Ser Gly Val
145                 150                 155                 160

Gln Ala Asn Asn Lys Leu Leu Tyr Asp Leu Ser Ala Met Arg Ala Asp
                165                 170                 175

Ile Gly Asp Met Arg Lys Tyr Ala Val Leu Val Tyr Ser Lys Asp Asp
                180                 185                 190

Ala Leu Glu Thr Asp Glu Leu Val Leu His Val Asp Ile Glu His Gln
            195                 200                 205

Arg Ile Pro Thr Ser Gly Val Leu Pro Val
210                 215
```

<210> SEQ ID NO 7
<211> LENGTH: 25
<212> TYPE: DNA
<213> ORGANISM: cucumber mosaic virus - PRIMER RMM351

<400> SEQUENCE: 7
cgtagaattc agtcgagcca tggac                                    25

<210> SEQ ID NO 8
<211> LENGTH: 28
<212> TYPE: DNA
<213> ORGANISM: cucumber mosaic virus - PRIMER RMM352

<400> SEQUENCE: 8
gaccactcga gccgtaagct ccatggac                                 28

<210> SEQ ID NO 9
<211> LENGTH: 974
<212> TYPE: DNA
<213> ORGANISM: cucumber mosaic virus strain C
<220> FEATURE:
<221> NAME/KEY: CDS
<222> LOCATION: (15)..(671)

<400> SEQUENCE: 9

```
aattgagtcg agtc atg gac aaa tct gaa tca acc agt gct ggt cgt aac    50
                Met Asp Lys Ser Glu Ser Thr Ser Ala Gly Arg Asn
                1               5                   10 cat cga cgt cgt ccg cgt cgt ggt tcc cgc tcc gcc ccc tcc tcc gcg    98
His Arg Arg Arg Pro Arg Arg Gly Ser Arg Ser Ala Pro Ser Ser Ala
```

|  |  |  |  |  |  |  |  |  |  |  |  |  |  |  |  |
|---|---|---|---|---|---|---|---|---|---|---|---|---|---|---|---|
|  |  | 15 |  |  |  | 20 |  |  |  | 25 |  |  |  |  |  |

```
gat gct aac ttt aga gtc ttg tcg cag cag ctt tcg cga ctt aat aag    146
Asp Ala Asn Phe Arg Val Leu Ser Gln Gln Leu Ser Arg Leu Asn Lys
     30                  35                  40 acg tta gca gct ggt cgt cca act att aac cac cca acc ttt gta ggg    194
Thr Leu Ala Ala Gly Arg Pro Thr Ile Asn His Pro Thr Phe Val Gly
 45                  50                  55                  60 agt gaa cgc tgt aga cct ggg tac acg ttc aca tct att acc cta aag    242
Ser Glu Arg Cys Arg Pro Gly Tyr Thr Phe Thr Ser Ile Thr Leu Lys
                     65                  70                  75 cca cca aaa ata gac cgt gag tct tat tac ggt aaa agg ttg tta cta    290
Pro Pro Lys Ile Asp Arg Glu Ser Tyr Tyr Gly Lys Arg Leu Leu Leu
             80                  85                  90 cct gat tca gtc acg gaa tat gat aag aag ctt gtt tcg cgc att caa    338
Pro Asp Ser Val Thr Glu Tyr Asp Lys Lys Leu Val Ser Arg Ile Gln
         95                 100                 105 att cga gtt aat cct ttg ccg aaa ttt gat tct acc gtg tgg gtg aca    386
Ile Arg Val Asn Pro Leu Pro Lys Phe Asp Ser Thr Val Trp Val Thr
    110                 115                 120 gtc cgt aaa gtt cct gcc tcc tcg gac tta tcc gtt gcc gcc atc tct    434
Val Arg Lys Val Pro Ala Ser Ser Asp Leu Ser Val Ala Ala Ile Ser
125                 130                 135                 140 gct atg ttc gcg gac gga gcc tca ccg gta ctg gtt tat cag tat gcc    482
Ala Met Phe Ala Asp Gly Ala Ser Pro Val Leu Val Tyr Gln Tyr Ala
                145                 150                 155 gca tct gga gtc caa gcc aac aac aaa ctg ttg ttt gat ctt tcg gcg    530
Ala Ser Gly Val Gln Ala Asn Asn Lys Leu Leu Phe Asp Leu Ser Ala
            160                 165                 170 atg cgc gct gat ata ggt gac atg aga aag tac gcc gtc ctc gtg tat    578
Met Arg Ala Asp Ile Gly Asp Met Arg Lys Tyr Ala Val Leu Val Tyr
        175                 180                 185 tca aaa gac gat gcg ctc gag acg gac gag cta gta ctt cat gtt gac    626
Ser Lys Asp Asp Ala Leu Glu Thr Asp Glu Leu Val Leu His Val Asp
    190                 195                 200 atc gag cac caa cgc att ccc aca tct gga gtg ctc cca gtc tga        671
Ile Glu His Gln Arg Ile Pro Thr Ser Gly Val Leu Pro Val
205                 210                 215 ttccgtgttc ccagaaccct ccctccgatc tctgtggcgg agctgagtt ggcagttcta    731 ctacaaactg tctggagtca ctaaacgttt tacggtgaac gggttgtcca tccagcttac    791
ggctaaaatg gtcagtcgtg gagaaatcca cgccagcaga tttacaaatc tctgaggcgc    851 cttttgaaacc atctcctagg tttcttcgga agggcttcgg tccgtgtacc tctagcgcaa    911
cgtgctagtt tcagggtacg ggtgcccccc cactttcgtg ggggcctcca aaaggagacc    971
aaa                                                                 974
```

<210> SEQ ID NO 10
<211> LENGTH: 218
<212> TYPE: PRT
<213> ORGANISM: cucumber mosaic virus strain C

<400> SEQUENCE: 10

```
Met Asp Lys Ser Glu Ser Thr Ser Ala Gly Arg Asn His Arg Arg Arg
1               5                   10                  15

Pro Ar

-continued

```
Gly Arg Pro Thr Ile Asn His Pro Thr Phe Val Gly Ser Glu Arg Cys
 50                  55                  60

Arg Pro Gly Tyr Thr Phe Thr Ser Ile Thr Leu Lys Pro Pro Lys Ile
 65                  70                  75                  80

Asp Arg Glu Ser Tyr Tyr Gly Lys Arg Leu Leu Leu Pro Asp Ser Val
                 85                  90                  95

Thr Glu Tyr Asp Lys Lys Leu Val Ser Arg Ile Gln Ile Arg Val Asn
                100                 105                 110

Pro Leu Pro Lys Phe Asp Ser Thr Val Trp Val Thr Val Arg Lys Val
            115                 120                 125

Pro Ala Ser Ser Asp Leu Ser Val Ala Ala Ile Ser Ala Met Phe Ala
130                 135                 140

Asp Gly Ala Ser Pro Val Leu Val Tyr Gln Tyr Ala Ala Ser Gly Val
145                 150                 155                 160

Gln Ala Asn Asn Lys Leu Leu Phe Asp Leu Ser Ala Met Arg Ala Asp
                165                 170                 175

Ile Gly Asp Met Arg Lys Tyr Ala Val Leu Val Tyr Ser Lys Asp Asp
                180                 185                 190

Ala Leu Glu Thr Asp Glu Leu Val Leu His Val Asp Ile Glu His Gln
            195                 200                 205

Arg Ile Pro Thr Ser Gly Val Leu Pro Val
210                 215
```

<210> SEQ ID NO 11
<211> LENGTH: 997
<212> TYPE: DNA
<213> ORGANISM: cucumber mosaic virus strain WL
<220> FEATURE:
<221> NAME/KEY: CDS
<222> LOCATION: (15)..(671)

<400> SEQUENCE: 11

```
gtcttagtgt gcct atg gac aaa tct gga tct ccc aat gct agt aga acc        50
                Met Asp Lys Ser Gly Ser Pro Asn Ala Ser Arg Thr
                 1               5                  10 tcc cgg cgt cgt cgc ccg cgt aga ggt tct cgg tcc gct tct ggt gcg        98
Ser Arg Arg Arg Arg Pro Arg Arg Gly Ser Arg Ser Ala Ser Gly Ala
         15                  20                  25 gat gca ggg ttg cgt gct ttg act cag cag atg ctg aaa ctc aat aga       146
Asp Ala Gly Leu Arg Ala Leu Thr Gln Gln Met Leu Lys Leu Asn Arg
 30                  35                  40 acc ctc gcc att ggt cgt ccc act ctt aac cac cca acc ttc gtg ggt       194
Thr Leu Ala Ile Gly Arg Pro Thr Leu Asn His Pro Thr Phe Val Gly
 45                  50                  55                  60 agt gaa agc tgt aaa ccc ggt tac act ttc aca tct att acc ctg aaa       242
Ser Glu Ser Cys Lys Pro Gly Tyr Thr Phe Thr Ser Ile Thr Leu Lys
                 65                  70                  75 ccg cct gaa att gag aaa ggt tca tat ttt ggt aga agg ttg tct ttg       290
Pro Pro Glu Ile Glu Lys Gly Ser Tyr Phe Gly Arg Arg Leu Ser Leu
             80                  85                  90 cca gat tca gtc acg gac tat gat aag aag ctt gtt tcg cgc att caa       338
Pro Asp Ser Val Thr Asp Tyr Asp Lys Lys Leu Val Ser Arg Ile Gln
         95                 100                 105 atc agg gtt aat cct ttg ccg aaa ttt gat tct acc gtg tgg gtt aca       386
Ile Arg Val Asn Pro Leu Pro Lys Phe Asp Ser Thr Val Trp Val Thr
    110                 115                 120 gtt cgg aaa gta cct tca tca tcc gat ctt tcc gtc gcc gcc atc tct       434
Val Arg Lys Val Pro Ser Ser Asp Leu Ser Val Ala Ala Ile Ser
125                 130                 135                 140
```

```
gct atg ttt ggc gat ggt aat tca ccg gtt ttg gtt tat cag tat gct      482
Ala Met Phe Gly Asp Gly Asn Ser Pro Val Leu Val Tyr Gln Tyr Ala
            145                 150                 155 gcg tcc gga gtt cag gcc aac aat aag tta ctt tat gac ctg tcc gag      530
Ala Ser Gly Val Gln Ala Asn Asn Lys Leu Leu Tyr Asp Leu Ser Glu
        160                 165                 170 atg cgt gct gat atc ggc gac atg cgt aag tac gcc gtc ctg gtt tac      578
Met Arg Ala Asp Ile Gly Asp Met Arg Lys Tyr Ala Val Leu Val Tyr
        175                 180                 185 tcg aaa gac gat aaa cta gag aag gac gag att gca ctt cat gtc gac      626
Ser Lys Asp Asp Lys Leu Glu Lys Asp Glu Ile Ala Leu His Val Asp
        190                 195                 200 gtc gag cat caa cga att cct atc tca cgg atg ctc ccg act tag           671
Val Glu His Gln Arg Ile Pro Ile Ser Arg Met Leu Pro Thr
205                 210                 215 tccgtgtgtt taccggcgtc cgagaacgtt aaactacact ctcaatcgcg agtgctgact    731
tggtagtatt gcttcaaact gcctgaagtc cctaaacgtg ttgttgcgcg gggaacgggt    791
gtccatccag cttacggcta aaatggtcgt gtctttcaca cgccgatgtc ttacaagatg    851
tcgagatacc cttgaaatca tctcctagat ttcttcggaa gggcttcgtg agaagctcgt    911
gcacggtaat acacttgata ttaccaagag tgcgggtatc gcctgtggtt ttccacaggt    971
tctccaggtt ctccataagg agacca                                          997
```

<210> SEQ ID NO 12
<211> LENGTH: 218
<212> TYPE: PRT
<213> ORGANISM: cucumber mosaic virus strain WL

<400> SEQUENCE: 12

```
Met Asp Lys Ser Gly Ser Pro Asn Ala Ser Arg Thr Ser Arg Arg Arg
1               5                   10                  15

Arg Pro Arg Arg Gly Ser Arg Ser Ala Ser Gly Ala Asp Ala Gly Leu
            20                  25                  30

Arg Ala Leu Thr Gln Gln Met Leu Lys Leu Asn Arg Thr Leu Ala Ile
        35                  40                  45

Gly Arg Pro Thr Leu Asn His Pro Thr Phe Val Gly Ser Glu Ser Cys
    50                  55                  60

Lys Pro Gly T

-continued

```
Arg Ile Pro Ile Ser Arg Met Leu Pro Thr
    210                 215

<210> SEQ ID NO 13
<211> LENGTH: 218
<212> TYPE: PRT
<213> ORGANISM: cucumber mosaic virus CMVQ3

<400> SEQUENCE: 13

Met Asp Lys Ser Gly Ser Pro Asn Ala Ser Arg Thr Ser Arg Arg Arg
1               5                   10                  15

Arg Pro Arg Arg Gly Ser Arg Ser Ala Ser Gly Ala Asp Ala Gly Leu
            20                  25                  30

Arg Ala Leu Thr Gln Gln Met Leu Arg Leu Asn Lys Thr Leu Ala Ile
        35                  40                  45

Gly Arg Pro Thr Leu Asn His Pro Thr Phe Val Gly Ser Glu Ser Cys
    50                  55                  60

Lys Pro Gly Tyr Thr Phe Thr Ser Ile Thr Leu Lys Pro Pro Glu Ile
65                  70                  75                  80

Glu Lys Gly Ser Tyr Phe Gly Arg Arg Leu Ser Leu Pro Asp Ser Val
                85                  90                  95

Thr Asp Tyr Asp Lys Lys Leu Val Ser Arg Ile Gln Ile Arg Ile Asn
            100                 105                 110

Pro Leu Pro Lys Phe Asp Ser Thr Val Trp Val Thr Val Arg Lys Val
        115                 120                 125

Pro Ser Ser Ser Asp Leu Ser Val Ala Ala Ile Ser Ala Met Phe Gly
    130                 135                 140

Asp Gly Asn Ser Pro Val Leu Val Tyr Gln Tyr Ala Ala Ser Gly Val
145                 150                 155                 160

Gln Ala Asn Asn Lys Leu Leu Tyr Asp Leu Ser Glu Met Arg Ala Asp
                165                 170                 175

Ile Gly Asp Met Arg Lys Tyr Ala Val Leu Val Tyr Ser Lys Asp Asp
            180                 185                 190

Lys Leu Glu Lys Asp Glu Ile Val Leu His Val Asp Val Glu His Gln
        195                 200                 205

Arg Ile Pro Ile Ser Arg Met Leu Pro Thr
    210                 215

<210> SEQ ID NO 14
<211> LENGTH: 772
<212> TYPE: DNA
<213> ORGANISM: cucumber mosaic virus - CMV-A35
<220> FEATURE:
<221> NAME/KEY: CDS
<222> LOCATION: (3)..(656)

<400> SEQUENCE: 14 cc atg gac aaa tct gaa tca acc agt gct ggt cgt aac cgt cga cgt      47
   Met Asp Lys Ser Glu Ser Thr Ser Ala Gly Arg Asn Arg Arg Arg
   1               5                   10                  15 cgt ccg cgt cgt ggt tcc cgc tcc gcc ctc tcc tcc gcg gat gct aac      95
Arg Pro Arg Arg Gly Ser Arg Ser Ala Leu Ser Ser Ala Asp Ala Asn
            20                  25                  30 ttt aga gtc ctg tcg cag cag ctt tcg cga ctt aat aag acg tta gca     143
Phe Arg Val Leu Ser Gln Gln Leu Ser Arg Leu Asn Lys Thr Leu Ala
        35                  40                  45 gct ggt cgt cca act att aac cac cca acc ttt gta ggg agt gaa cgc     191
Ala Gly Arg Pro Thr Ile Asn His Pro Thr Phe Val Gly Ser Glu Arg
```

```
            50                  55                  60
tgt aga cct ggg tac acg ttc aca tct att acc cta aag cca cca aaa    239
Cys Arg Pro Gly Tyr Thr Phe Thr Ser Ile Thr Leu Lys Pro Pro Lys
 65                  70                  75 ata gac cgt ggg tct tat tac ggt aaa agg ttg tta cta cct gat tca    287
Ile Asp Arg Gly Ser Tyr Tyr Gly Lys Arg Leu Leu Leu Pro Asp Ser
 80                  85                  90                  95 gtc aca gaa tat gat aag aag ctt gtt tcg cgc att caa att cga gtt    335
Val Thr Glu Tyr Asp Lys Lys Leu Val Ser Arg Ile Gln Ile Arg Val
                    100                 105                 110 aat cct ttg ccg aaa ttt gat tct acc gtg tgg gtg aca gtc cgt aaa    383
Asn Pro Leu Pro Lys Phe Asp Ser Thr Val Trp Val Thr Val Arg Lys
                115                 120                 125 gtt cct gcc tcc tcg gac tta tcc gtt gcc gcc atc tct gct atg ttc    431
Val Pro Ala Ser Ser Asp Leu Ser Val Ala Ala Ile Ser Ala Met Phe
            130                 135                 140 gcg gac gga gcc tca ccg gta ctg gtt tat cag tat gcc gca tct gga    479
Ala Asp Gly Ala Ser Pro Val Leu Val Tyr Gln Tyr Ala Ala Ser Gly
        145                 150                 155 gtc caa gcc aac aac aaa ctg ttg tat gat ctt tcg gcg atg cgc gct    527
Val Gln Ala Asn Asn Lys Leu Leu Tyr Asp Leu Ser Ala Met Arg Ala
160                 165                 170                 175 gat ata ggt gac atg aga aag tac gcc gtc ctc gtg tat tca aaa gac    575
Asp Ile Gly Asp Met Arg Lys Tyr Ala Val Leu Val Tyr Ser Lys Asp
                    180                 185                 190 gat gcg ctc gag acg gac gag cta gta ctt cat gtt gac atc gag cac    623
Asp Ala Leu Glu Thr Asp Glu Leu Val Leu His Val Asp Ile Glu His
                195                 200                 205 caa cgc att ccc acg tct gga gtg ctc cca gtc tgattctgtg ttcccagaac  676
Gln Arg Ile Pro Thr Ser Gly Val Leu Pro Val
            210                 215 cctccctccg atctctgtgg cgggagctga gttggcagtt ctgctgtaaa ctgtctgaag  736
tcactaaacg ttttacggtg aacgggttgt ccatgg                            772

<210> SEQ ID NO 15
<211> LENGTH: 218
<212> TYPE: PRT
<213> ORGANISM: cucumber mosaic virus - CMV-A35

<400> SEQUENCE: 15

Met Asp Lys Ser Glu Ser Thr Ser Ala Gly Arg Asn Arg Arg Arg
1               5                   10                  15

Pro Arg Arg Gly Ser Arg Ser Ala Leu Ser Ser Ala Asp Ala Asn Phe
                20                  25                  30

Arg Val Leu Ser Gln Gln Leu Ser Arg Leu Asn Lys Thr Leu Ala Ala
            35                  40                  45

Gly Arg Pro Thr Ile Asn His Pro Thr Phe Val Gly Ser Glu Arg Cys
        50                  55                  60

Arg Pro Gly Tyr Thr Phe Thr Ser Ile Thr Leu Lys Pro Pro Lys Ile
65                  70                  75                  80

Asp Arg Gly Ser Tyr Tyr Gly Lys Arg Leu Leu Leu Pro Asp Ser Val
                85                  90                  95

Thr Glu Tyr Asp Lys Lys Leu Val Ser Arg Ile Gln Ile Arg Val Asn
            100                 105                 110

Pro Leu Pro Lys Phe Asp Ser Thr Val Trp Val Thr Val Arg Lys Val
        115                 120                 125

Pro Ala Ser Ser Asp Leu Ser Val Ala Ala Ile Ser Ala Met Phe Ala
```

-continued

```
                    130                 135                 140
Asp Gly Ala Ser Pro Val Leu Val Tyr Gln Tyr Ala Ala Ser Gly Val
145                 150                 155                 160

Gln Ala Asn Asn Lys Leu Leu Tyr Asp Leu Ser Ala Met Arg Ala Asp
                165                 170                 175

Ile Gly Asp Met Arg Lys Tyr Ala Val Leu Val Tyr Ser Lys Asp Asp
                180                 185                 190

Ala Leu Glu Thr Asp Glu Leu Val Leu His Val Asp Ile Glu His Gln
            195                 200                 205

Arg Ile Pro Thr Ser Gly Val Leu Pro Val
        210                 215

<210> SEQ ID NO 16
<211> LENGTH: 21
<212> TYPE: PRT
<213> ORGANISM: Cucumber Mosaic Virus - CMV-A35

<400> SEQUENCE: 16

Phe Cys Val Pro Arg Thr Leu Pro Pro Ile Ser Val Ala Gly Ala Glu
1               5                   10                  15

Leu Ala Val Leu Leu
            20

<210> SEQ ID NO 17
<211> LENGTH: 2
<212> TYPE: PRT
<213> ORGANISM: Cucumber Mosaic Virus - CMV-A35

<400> SEQUENCE: 17

Thr Val
1

<210> SEQ ID NO 18
<211> LENGTH: 2
<212> TYPE: PRT
<213> ORGANISM: Cucumber Mosaic Virus - CMV-A35

<400> SEQUENCE: 18

Ser His
1

<210> SEQ ID NO 19
<211> LENGTH: 10
<212> TYPE: PRT
<213> ORGANISM: Cucumber Mosaic Virus - CMV-A35

<400> SEQUENCE: 19

Thr Phe Tyr Gly Glu Arg Val Val His Gly
1               5                   10

<210> SEQ ID NO 20
<211> LENGTH: 218
<212> TYPE: PRT
<213> ORGANISM: cucumber mosaic virus - MAJORITY

<400> SEQUENCE: 20

Met Asp Lys Ser Glu Ser Thr Ser Ala Gly Arg Asn Arg Arg Arg Arg
1               5                   10                  15

Pro Arg Arg Gly Ser Arg Ser Ala Ser Ser Ala Asp Ala Asn Phe
            20                  25                  30

Arg Val Leu Ser Gln Gln Leu Ser Arg Leu Asn Lys Thr Leu Ala Ala
```

-continued

```
                35                  40                  45
Gly Arg Pro Thr Ile Asn His Pro Thr Phe Val Gly Ser Glu Arg Cys
    50                  55                  60
Lys Pro Gly Tyr Thr Phe Thr Ser Ile Thr Leu Lys Pro Pro Lys Ile
65                  70                  75                  80
Asp Arg Gly Ser Tyr Tyr Gly Lys Arg Leu Leu Leu Pro Asp Ser Val
                85                  90                  95
Thr Glu Tyr Asp Lys Lys Leu Val Ser Arg Ile Gln Ile Arg Val Asn
            100                 105                 110
Pro Leu Pro Lys Phe Asp Ser Thr Val Trp Val Thr Val Arg Lys Val
        115                 120                 125
Pro Ala Ser Ser Asp Leu Ser Val Ala Ala Ile Ser Ala Met Phe Ala
    130                 135                 140
Asp Gly Ala Ser Pro Val Leu Val Tyr Gln Tyr Ala Ala Ser Gly Val
145                 150                 155                 160
Gln Ala Asn Asn Lys Leu Leu Tyr Asp Leu Ser Ala Met Arg Ala Asp
                165                 170                 175
Ile Gly Asp Met Arg Lys Tyr Ala Val Leu Val Tyr Ser Lys Asp Asp
            180                 185                 190
Ala Leu Glu Thr Asp Glu Leu Val Leu His Val Asp Ile Glu His Gln
        195                 200                 205
Arg Ile Pro Thr Ser Gly Val Leu Pro Val
    210                 215
```

<210> SEQ ID NO 21
<211> LENGTH: 770
<212> TYPE: DNA
<213> ORGANISM: cucumber mosaic virus - MAJORITY

<400> SEQUENCE: 21

```
ccatggacaa atctgaatca accagtgctg gtcgtaaccg tcgacgtcgt ccgcgtcgtg    60
gttcccgctc cgcccctcc tccgcggatg ctaactttag agtcttgtcg cagcagcttt   120
cgcgacttaa taagacgtta gcagctggtc gtccaactat taaccaccca acctttgtag   180
ggagtgaacg ctgtagacct gggtacacgt tcacatctat taccctaaag ccaccaaaaa   240
tagaccgtgg gtcttattac ggtaaaaggt tgttattacc tgattcagtc acggaatatg   300
ataagaagct tgtttcgcgc attcaaattc gagttaatcc tttgccgaaa tttgattcta   360
ccgtgtgggt gacagtccgt aaagttcctg cctcctcgga cttatccgtt gccgccatct   420
ctgctatgtt cgcggacgga gcctcaccgg tactggttta tcagtatgct gcatctggag   480
tccaagctaa caacaaattg ttgtatgatc tttcggcgat gcgcgctgat ataggtgaca   540
tgagaaagta cgccgtcctc gtgtattcaa agacgatgc gctcgagacg gacgagctag   600
tacttcatgt tgacatcgag caccaacgca ttcccacgtc tggggtgctc ccagtctgat   660
tctgtgttcc cagaaccctc cctccgattt ctgtggcggg agctgagttg gcagttctgc   720
tataaactgt ctgaagtcac taaacgtttt acggtgaacg ggttgtccat              770
```